(12) United States Patent
Christgau et al.

(10) Patent No.: US 7,632,684 B2
(45) Date of Patent: Dec. 15, 2009

(54) ASSAY OF ISOMERISED AND/OR OPTICALLY INVERTED PROTEINS AND PROTEIN FRAGMENTS

(75) Inventors: Stephan Christgau, Gentofte (DK); Dennis B. Henriksen, Alleroed (DK); Paul A. C. Cloos, København (DK)

(73) Assignee: Nordic Bioscience Diagnostics A/S, Herlev (DK)

( * ) Notice: Subject to any disclaimer, the term of this patent is extended or adjusted under 35 U.S.C. 154(b) by 211 days.

(21) Appl. No.: 10/478,451

(22) PCT Filed: May 22, 2002

(86) PCT No.: PCT/EP02/05612

§ 371 (c)(1),
(2), (4) Date: May 24, 2004

(87) PCT Pub. No.: WO02/095415

PCT Pub. Date: Nov. 28, 2002

(65) Prior Publication Data

US 2004/0259172 A1    Dec. 23, 2004

(30) Foreign Application Priority Data

May 23, 2001    (GB) .................... 0112626.7

(51) Int. Cl.
   G01N 33/00    (2006.01)
   G01N 33/53    (2006.01)
(52) U.S. Cl. ................... 436/90; 435/7.1; 530/840
(58) Field of Classification Search .............. None
See application file for complete search history.

(56) References Cited

U.S. PATENT DOCUMENTS 6,107,047 A    8/2000 Fledelius et al. ........... 435/7.1
6,849,594 B1 *    2/2005 Chen et al. ................. 514/2

FOREIGN PATENT DOCUMENTS

FR    WO 01/05422 A2    1/2001
WO    WO 96/30765    10/1996
WO    WO 98/39653    9/1998

OTHER PUBLICATIONS

Vilim et al. "Characterization of Monoclonal Antibodies Recognizing Different Fragments of Cartilage Oligomeric Matrix Protein in Human Body Fluids" Archives of Biochemistry and Biophysics 341, 8-16, 1997.*
van den Oetelaar et al. "Analysis of aspartic acid racemization; Evaluation of a chiral capillary gas chromatographic and a diastereomeric high-performance liquid chromatographic method" J Chromatogr. Feb. 13, 1987;388(2):441-7.*
Wolfe, S.L., Molecular and Cellular Biology, 1993, pp. 790-793.*
Kuby et al. Immunology, W.H. Freeman and Company (1992), p. 125.*
Bendayan, M. J. Histochem. Cytochem. 1995; 43:881-886.*
Bost et al. Immunol. Invest. 1988; 17:577-586.*
Arikawa-Hirasawa, et al. "Perlecan is essential for cartilage and cephalic development" Nature Genetics, Nature America, New York, U.S., vol. 23, No. 3, Nov. 1999, pp. 354-358, XP001034683.
Costell, et al., "Perlecan Maintains the Integrity of Cartilage and Some Basement Membranes" The Journal of Cell Biology, Rockefeller University Press, U.S., vol. 147, No. 5, Nov. 29, 1999, pp. 1109-1122, XP002906976.
International Search Report dated Feb. 1, 2004 issued in corresponding application No. PCT/EP02/05612.
Adams, "The Thrombospondin Type 1 Repeat (TSR) Superfamily: Diverse Proteins With Related Roles in Neuronal Development", Dev Dyn. (2000) 218: 280-299.
Clark et al., "Serum Cartilage Oligomeric Matrix Protein Reflects Osteoarthritis Presence and Severity", the Johnston County Osteoarthritis Project, Arthritis Rheum (1999) 42: 2356-2364.
Clarke, "Propensity for Spontaneous Succinimide Formation from Aspartyl and Asparaginyl Residues in Cellular Proteins", Int. J. Peptide Protein Res. (1987) 30:808-821.
Costell et al., "Perlecan Maintains the Integrity of Cartilage and Some Basement Membranes", J Cell Biol. (1999) 147:1109-1122.
Dodge et al., "Osteoarthritis and Cartilage", Osteoarthritis Cartilage (1998) 6, 435-440.
Eyre, "The Collagens of Articular Cartilage", Semin. Arthritis Rheum. 21 (suppl. 2): 2-11, 1991.
Flannerly et al., "Identification of a Stromelysin Cleavage with the Interglobular Domain of Human Aggrecan", J Biol. Chem. (1992) 267: 1008-1014.
Fledeluis et al., "Characterization of Urinary Degradation Products Derived from Type 1 Collagen. Identification of a $\beta$-Isomerized Asp-Gly sequence within the C-telopeptide ($\alpha$1) region", J Biol. Chem. (1997) 275:9755-9763.
Ganu at al., "Inhibition of Interleukin-1$\alpha$-Induced Cartilage Oligomeric Matrix Protein Degradation in Bovine Articular Cartilage by matrix Metalloproteinase Inhibitors", Arthritis Rheum (1998) 41:2143-2151.
Geiger et al., "De-amidation, Isomerization, and Racemization at Asparaginyl and Aspartyl Residues in Peptides", J Biol. Chem. (1987) 262(2):785-794.
Hardingham et al., "Proteoglycans: Many Forms and Many Functions" FASEB J (1992)6:861-870.

(Continued)

*Primary Examiner*—Christopher L Chin
*Assistant Examiner*—Christine Foster
(74) *Attorney, Agent, or Firm*—Gregory B. Butler, Esq.; Edwards Angell Palmer & Dodge LLP

(57) ABSTRACT

In an in vitro diagnostic test for osteoarthritis or rheumatoid arthritis, the amount or presence in a sample of anisomerised or optically inverted protein fragment is measured which derives from perlecan, bigylcan, decorin, fibrillin-1 or protocadherin or which is a specific sequence from aggrecan, type II collagen, COMP or CILP.

5 Claims, 4 Drawing Sheets

OTHER PUBLICATIONS

Hardingham et al., "The Specific Interation of Lyaluronic acid with cartilage proteoglycans", Biochim Biophys Acta (1972) 279:401-405.

"Chondrex: New Marker of Joint Disease", Clin. Chem (1998) 44:509-516, Harvey et al.

Heinegard et al., "A Method for the Quantification of Cartilage Proteoglycan Structures Liberated to the Synovial Fluid During Developing Degenerative Joint Disease", Scand J Clin Lab Invest (1985) 45:421-427.

Heinegard et al., "Noncollagenous Proteins; Glycoproteins and Related Proteins" Dynamics of Bone and Cartilage Metabolism, Academic Press, NY (1999) pp. 59-69.

Hermanson, "Bioconjugate Techniques" Academic Press (1996) San Diego, USA, pp. 194-196.

Inerot et al, "Articular-Cartilage Proteoglycans in Aging and Osteoarthritis", Glycoconjugates vol. IV, Academic Press, NU (1982) pp. 335-355.

Johansen et al., "A New Biochemical Marker for Joint Injury. Analysis of YKL-40 in Serum and Synovial Fluid", Br. J. Rheumatol (1993) 32:949-955.

Johansen et al., "Serum YKL-40 Levels in Healthy Children and Adults. Comparison with Serum and Synovial Fluid Levels of YKL-40 in Patients with Osteoarthrltis or Trauma of the Knee Joint", Br. J. Rheumatol. (1996) 35:553-559.

Kudson et al., "Cartilage Proteoglycans" Semin. Cell Dev. Biol. (2001) 12:69-78.

Lorenzo et al., "A Novel Cartilage Protein (CILP) Present in the Mid-zone of Human Articular Cartilage Increases with Age" J. Biol. Chem. (1998a) 273(36):23463-23468.

Lorenzo et al., "Cloning and Deduced Amino Acid Sequence of a Novel Cartilage Protein (CILP) Identifies a Proform Including a Nucleotide Pyrophosphohydrolase" J. Biol. Chem, 273(36):23469-23475, 1998.

Niedhart et al., "Small Fragments of Cartilage Oligomeric Matrix Protein in Synovial Fluid and Serum as Markers for Cartilage Degradation" Br. J. Rheumatol. 36:1151-1160, 1997.

Poole et al., "Biological Markers in Rheumatoid Arthritis" Sem. Arthr. Rheum. (1994) 23:17-31.

Poole et al, Methods for Evaluating Mechanisms of Cartilage Breakdown Cartilage Breakdown: Basic and Clinical Aspects, Marcel Dekker, New York, (1993) 225-260.

Radkiewicz et al., "Accelerated Racemization of Aspartic Acid and Asparagine Residues via Succinimide Intermediates: An ab Initio Theoretical Exploration of Mechanism" J. Am. Chem. Soc. (1996) 118:9148-9155.

Rafferty et al., "Pharmacokinetic Evaluation of Superactive Analogues of Growth Hormone-Releasing Factor (1-29)-Amide" Peptides (1988) 9(1):207-9.

Rosenberg et al, "Cartilage Oligomeric Metrix Protein Shows High Affinity Zinc-dependent Interaction with Triple Helical Collagen" J. Biol. Chem (1998) 273:20397-20403.

Saxne et al., "Cartilage Oligomeric Matrix Protein: A Novel Marker of Cartilage Turnover Detectable in Synovial Fluid and Blood" Br. J. Rheumatol. (1992) 31: 583-591.

Saxne et al., "Concise Communications—Serum Concentrations of Two Cartilage Matrix Proteins Reflecting Different Aspects of Cartilage Turnover in Relapsing Polychondritis" Arthritis Rheum (1995) 38:294-296.

Van Der Rest et al., "Collagen Family of Proteins" FASEB J (1991) 5:2814-2823.

Van Regenmortel et al., "D-peptides as Immunogens and Diagnostic Reagents" Current Opinion in Biotechnology (1998) 9:377-382.

Vingsbo-Lundberg et al., "Increased Serum Levels of Cartilage Oligomeric Matrix Protein in Chronic Erosive Arthritis in Rats"Arthritis Rheum (1998) 41:544-550.

Wollheim, et al., "Predictors of Joint Damage in Rheumatoid Arthritis" APMIS (1996) 104:81-93.

Sakai, et al., "Fillbrillin, A New 350-kD Glycoprotein, Is a Component of Extracellular Microfibrils" J Cell Biol (Dec. 1986) 103 (6 Pt 1): 2499-509.

Keene et al., "Fibrillin-1 in Human Cartilage: Developmental Expression and Formation of Special Banded Fibers" J. Histochem Cytochem (Aug. 1997) 45(8):1069-82.

Zhang et al., "Developmental Expression of Fibrillin Genes Suggests Heterogeneity of Extracellular Microfibrils" J Cell Biol (May 1995) 129(4)1165-76.

Didonato et al., "Selective Deamidation of Ribonuclease A" J Biol Chem (1993) 268:4745-4751.

Stevenson at al., "Comparison of Separation and Detection Techniques for Human Growth Hormone Releasing Factor (hGRF) and the Products Derived from Deamidation" J Pharm Biomed Anal (1993) 11:367-373.

Aswad et al., "Methods for Analysis of Deamidation and Isoaspartate Formation in Peptides and Proteins" CRC Series in anaytical Biotechnology (1995) CRC Press, Boca Raton, FL; Ch. 2, pp. 7-29.

Aswad et al., "Modification of Synetic Peptides Related to Lactate Dehydrogenase (231-242) by Protein Carboxyl Methyltransferase and Tyrosine Protein Kinase: Effects of Introducing an Isopeptide Bond between Aspartic Acid-235 and Serine 236" (1987) Biochemistry 26: 675-681.

Potter et al., "In Vitro Aging of Calmodulin Generates Isoaspartate at Multiple Asn-Gly and Asp-Gly Sites in Calcium-Binding Domains II, III, and IV" (1993) Protein Sci 2: 1648-1663.

Smyth et al., "The Sequence of Amino Acid Residues in Bovine Pancreatic Ribonuclease: Revisions and Confirmations" (1963) J Biol Chem 238:227-234.

* cited by examiner

Panel A

Panel B

ASSAY OF ISOMERISED AND/OR OPTICALLY INVERTED PROTEINS AND PROTEIN FRAGMENTS

The present application claims benefit to PCT/EP02/05612 (WO 02/095415) as filed on May 22, 2002 which application claims benefit to Great Britain Application No. 0112626.7 as filed on May 23, 2001. The disclosures of the PCT/EP02/05612 (WO 02/095415) and 0112626.7 are incorporated herein by reference.

BACKGROUND OF THE INVENTION

The present invention relates to immunoassays for non-collagen cartilage proteins and their fragments in biological samples such as body fluids. Such proteins and protein fragments may serve as an index of joint disease.

A number of diseases are associated with increased turnover of the extra cellular matrix of tissues or organs in the mammalian body. As examples of such diseases or pathological conditions, arthritic diseases involves increased turnover of tissues of the joint, osteoporosis is associated with increased turnover of bone tissue, psoriasis and scleroderma is associated with increased turnover of skin and various cancer types are also associated with increased tissue turnover of the disease affected tissue(s) or organ(s). Of special relevance in these conditions is a quantification of the catabolic processes associated with the disease as these often predominates and results in degradation of the affected tissues or organs. Such catabolic process can be difficult to quantify, and specific biochemical markers for monitoring such processes would be of great clinical utility for diagnosis, monitoring and assessing prognosis of the diseases. Furthermore, such markers could be used in pre-clinical and clinical research for identification and assessment of new therapeutic agents and for optimising treatment dose and treatment modality. However, even though a need for such markers clearly exists it has been difficult to identify and develop such biochemical markers and very few such markers exist today for routine use in clinical management of disease or research into disease mechanisms and development of new therapeutic agents.

The present invention provides a general method for identification of biochemical markers specific for catabolic processes in a mammalian tissue or organ. This method has been applied for identification of new markers of cartilage turnover; a process which is of relevance for all arthritic diseases, as described below.

Increased awareness of the early biochemical and structural changes in cartilage-related diseases in combination with the introduction of new disease suppressive agents has created the need to develop improved tools to assess disease severity and prognosis. Thus the need for sensitive simple and reliable markers for cartilage degradation is evident, and such markers will fulfill important clinical purpose for management of arthritic disease.

As of today, no tissue specific biochemical marker exists which is of general use for diagnosis and monitoring of cartilage degradation in Rheumatoid Arthritis (RA) and Osteoarthritis (OA) patients. Markers such as C-reactive protein (CRP), rheumatoid factor (RF) and erythrocyte sedimentation rate (ESR) are frequently applied in RA. These markers provide information about the inflammatory reactions in the disease, but are not specific for joint diseases, and in spite of their wide-spread use, their clinical utility is still discussed.

At present one of the best ways to obtain information about the status of the (individual) joints in arthritis patients is radiological examination.

Measurement of metabolites, such as hyaluronates and aggrecan fragments arising from destruction of the specific organ (the joints) affected by the arthritis has been reported, for review please see Wollheim (Wollheim, 1996). The two main arthritic diseases, RA and OA are briefly described below.

Osteoarthritis:

Osteoarthritis (OA) is a chronic disease characterized by degenerative changes of the joints and bone with destruction of the cartilage and reactive formation of bone in the periphery of the joint. OA is a common disease, with an increasing incidence with age. At the age of 50 approximately 20% have symptoms of OA and radiologically almost 90% exhibit OA-related changes.

One of the earliest events that can be detected histologically is the loss of proteoglycans (aggrecan) from the tissue (Flannerly et al 1992). The likely mechanism is the fragmentation of aggrecan by proteinases. The generation of aggrecan fragments is detrimental to the proper functioning of cartilage. In later stages of the disease also collagen fibrils are degraded (Eyre et al 1991) and the surface of the cartilage is eroded due to loss of tissue (Inerot & Heinegård, 1982).

Rheumatoid Arthritis:

Rheumatoid arthritis (RA) is an autoimmune disease, where the patients own immune system attacks the joints, causing inflammation and subsequent degradation of the cartilage matrix. The disease affects approximately 1% of the population. At present the underlying causes responsible for initiation of the disease are unknown, however studies of its epidemiology show that genetic as well as environmental factors contribute to the pathogenesis.

RA is characterized by chronic inflammation associated with erosion of both cartilage and bone. In advanced late stages of the disease, radiographs show characteristic evidence of cartilage loss and bone erosion at the joint margin. However much damage may be done early in the disease, before radiographs change. Sensitive indices of the current cartilage and bone changes in RA would therefore be of potential value to clinicians.

The present invention describes methods for identifying such markers and also methods for developing and applying assays for such markers for management of arthritic disease as well as for developing new therapeutic or disease management methods for arthritic disease.

One aim of the present invention is to provide new methods and procedures for identifying potential markers of cartilage degradation based on identification of isomerised and/or optically inverted fragments of cartilage-derived proteins. Such markers will provide a significant advantage for the clinical management of OA, RA as well as other diseases affecting joint metabolism. Furthermore the use of such markers for management of arthritic disease and development of anti-arthritic therapeutic agents is described.

The Extracellular Matrix of Cartilage:

Cartilage matrix is synthesized, degraded, organized and maintained by a sparse population of chondrocytes (making up 0.5-2% of the total cartilage volume) (Poole et al 1994, Poole & Dieppe 1994). These cells are protected from the potentially damaging forces of mechanical function by the extra-cellular matrix (ECM) they produce.

The properties of cartilage are critically dependent upon the structure and integrity of the ECM. Thus, normal turnover is a conservative process in which the rate of matrix degradation does not exceed the rate at which it is replaced. There is a slow constant turnover of the ECM with chondrocytes both degrading and synthesizing matrix proteins. Healing of cartilage is dependent entirely on surviving chondrocytes near the margins of the injury. In adults these cells mediate essentially no repair.

A number of cartilage proteins have been identified and characterized. The main structural component of cartilage is made up of collagen fibers, predominantly composed of collagen type II with minor amounts (typically less than 10%) of collagen type IX and type XI. Interspaced between the collagen network are long chains of the negatively charged polysaccharide hyaluronic acids, to which several large proteoglycans are attached. The major proteoglycan is aggrecan. Aggrecan is a large protein with a molecular mass of 2600 kDa with a core protein of 220 kDa (Doege et al 1991). The protein is composed of 93% glycosaminoglycans (about 87% chondroitin sulphate and 6% keratan sulphate) and 7% protein. Aggrecan is a major component of cartilage where it accounts for about 10% of the dry weight of cartilage. The oligosaccharide moieties of aggrecan are highly negatively charged which draws water into the tissue as it creates a large osmotic swelling pressure. The water thus swells and expands the aggrecan-rich matrix. This places the collagen network under tension and an equilibrium is achieved when tension in the collagen network balances the swelling pressure (i.e., when no more water enters the tissue because the force is insufficient to stretch the collagen network any further). The aggrecan molecule is made up of 7 different domains. At the N-terminus there are two structurally related globular domains termed G1 and G2, separated by a short region known as the interglobular domain (IGD). Although the function of the G2 domain has not been determined the G1 domain is known to serve as a 'linker' to hyaluronan and is responsible for the formation of large aggrecan aggregates (Hardingham & Muir, 1972). The G1 domain is also in contact with cartilage link protein (see below). C-terminally to the G2 domain there is a long region consisting of two glycosaminoglycan-rich regions. The first is a domain rich in keratan sulphate (KS), whereas the other is composed of two domains rich in chondroitin sulphate (CS). At the C-terminus aggrecan possesses a third globular domain G3. The G3 domain seems to be lost soon after synthesis and secretion, the consequence of loss of the G3 domain is not yet understood (Hardingham & Fosang, 1992). Current evidence indicates that aggrecan fragments released during degradation of the cartilage matrix are heterogeneous products and may reflect various stages of disease progression depending on which fragments are monitored. In early or non-cartilage destructive diseases no or only small amounts of fragments related to the G1 domain are released (Saxne & Heinegård 1992). Increased release of G1 related fragments, only accompanies the more profound and presumably irreversible cartilage derangement seen in patients with more damaged joints (Saxne & Heinegård 1995).

A number of non-collagen cartilage proteins have been described although not all of these proteins are specific in cartilage, they play important structural and/or functional roles in the tissue, and may potentially serve as markers of cartilage turnover.

Cartilage intermediate layer protein (CILP) is noncollagenous cartilage protein composed of a single polypeptide chain with a molecular weight of 91.5 kDa, including N-linked oligosaccharides (Lorenzo et al. 1998a and 1998b). The protein is synthesized by chondrocytes and located to the interterritorial cartilage. It is neither found in the superficial nor deepest regions of the articular cartilage. CILP has been reported to increase with age and has been suggested to be a marker of early OA.

Cartilage Oligomeric Matrix Protein (COMP) is a non-collagenous extra-cellular matrix protein found predominantly in cartilage, but also in tendon, ligament and meniscus (Muller et al 1998). Several mesenchymal cells including synoviocytes and dermal fibroblasts produce substantial amounts of COMP (Dodge et al 1998). The physiological function of the protein is not known. COMP is a large disulfide-linked pentameric protein with a molecular weight of each monomer of about 100 kDa. The protein belongs to the thrombospondin family and it displays a high homology to thrombospondin 1-4 (Adams & Tucker 2000). In vitro data indicate that COMP may mediate cell binding within the cartilage matrix in accordance with the function of other members of the thrombospondin family. Furthermore, it is likely that COMP participates in regulation of collagen fibril formation (Rosenberg et al 1998). The major source of COMP within the joint appears to be fibroblastic cells in sub-synovial tissue. In cartilage COMP may be found as both the intact pentamer and in various fragments (43-160 kDa) generated by the action of MMP's as well as other proteases (Saxne & Heinegård 1992, Ganu et al 1998). In OA cartilage the proportion of degraded COMP is higher than in normal cartilage even though the total amounts of COMP appears to be similar (Vilim et al 1997, Niedhart et al 1997). In RA cartilage there is a net loss of COMP, and the COMP fragments appear to be of smaller size than those seen in OA (Clarke et al 1999, Vingsbo-Lundberg et al 1998).

A number of COMP assays based on both polyclonal and monoclonal antibodies have been described in the literature, but the exact epitope specificity of the assays is generally not characterized (Saxne & Heinegård 1992, Niedhart et al 1997). A number of cross-sectional studies have demonstrated elevated COMP levels in patients with OA, RA and other diseases affecting joint metabolism (Sharif et al 1995, Vingsbo-Lundberg et al 1998, Clarke et al 1999, Niedhart et al 1997).

Perlecan is a heparin sulphate proteoglycan that is expressed in all basement membranes, cartilage and several other mesenchymal tissues during development. Perlecan binds growth factors and interacts with various extracellular matrix proteins and cell adhesion molecules. Relatively high levels of perlecan have been found in mature cartilage, and in vitro experiments have suggested that perlecan supports chondrocyte differentiation (Costell et al 1999).

Biglycan and decorin belong to the family of small leucine rich proteoglycans. They are relatively highly expressed in foetal cartilage, but are found in lower amounts in adult cartilage. Their functional role in cartilage is not fully elucidated but they may be involved in maintaining the structural integrity of the collagen fiber network and the hyaluronic acid mesh (Knudson & Knudson 2001). Furthermore they may play a role in chondrogenesis and cartilage degradation.

Fibrillin-1 (Fib-1) is a connective tissue protein, with an estimated molecular mass of 350,000 D. Fibrillin 1 is found in extracellular microfibrils in a variety of connective tissues. The protein has a widespread distribution in the connective tissue matrices of skin, lung, kidney, vasculature, cartilage, tendon, muscle, cornea, and ciliary zonule (Sakai et al 1986). The functional relationships between this glycoprotein and other components of the microfibrils and elastic fibers are unknown. Synthesis of fibrillin-1 correlates with late morphogenesis and the appearance of well-defined organ structures (Zhang and Ramirez 1995). It is widely expressed in developing limbs and digits, especially in the perichondrium (Keene et al 1997). Fib-1 appears as a loose meshwork of fibers within cartilage matrix by 20 weeks of fetal gestation. Until early adolescence, Fib-1 forms loose bundles of microfibrils within cartilage (Keene et al; 1997). However, by late adolescence, broad banded fibers composed of Fib-1 are found accumulated pericellularly within cartilage probably as laterally packed and crosslinked microfibrils. It has been proposed that fibrillin-1 provides force-bearing structural support to extracellular microfibrils and that it may growth-regulating functions in the perichondrium (Keene et al. 1997, Zhang and Ramirez 1995).

Protocadherins constitute a large family belonging to the cadherin superfamily and function in different tissues of a wide variety of multicellular organisms. Protocadherins have unique features that are not found in classic cadherins. Little is known about the Protocadherin subfamily gamma.

In joint diseases, the rate of degradation of matrix often exceeds the rate of synthesis, and, as consequence, the tissue becomes thin and mechanically weak (Heinegård et al 1999). As the catabolic processes dominate in the arthritic disease states, fragments of cartilage proteins is produced, and such fragments can be measured in synovial fluid, serum and urine as markers of the cartilage degradation.

Joint diseases and related conditions involving abnormalities in the metabolism of cartilage cause widespread disability. Erosion of the articular cartilage is a typical finding in degenerative and inflammatory joint diseases, such as OA and RA.

BRIEF SUMMARY OF THE INVENTION

Hypothesis Underlying the Invention

This invention describes a novel approach for identifying markers of cartilage degradation, and for development of diagnostic and prognostic assays for monitoring joint diseases. This approach is applicable not only for the identification of cartilage derived biochemical markers, but also as a generally applicable method for identification of proteins or protein fragments of an extra-cellular matrix tissue or organ of a mammal that may be suited as markers for turnover of the specific tissue or organ. We show that specific components of articular cartilage are prone to isomerisation and optical inversion (Example 1) and we identify specific isomerisation/optical inversion prone sites in several cartilage proteins. We also demonstrate that isomerised and/or optically inverted fragments of cartilage protein are found in circulation, and that measurements of such fragments provide an index of joint cartilage degradation.

Aspartic acid and asparagine (Asx) and glutamic acid and glutamine (Glx) residues will in some susceptible proteins undergo a spontaneous re-arrangement where the normal peptide bond between the Asx or Glx residue and the adjacent residue is transferred from the normal α-carboxyl group to the β-carboxyl group (α-carboxyl group for the Glx residues) of the side chain (Clarke 1987). The isomerisation reaction proceeds via a succinimide intermediate, which upon spontaneous hydrolysis may result in one of four forms: the normally occurring αL, the isoform βL, or the two optically inverted forms αD and βD as outlined in the following reaction scheme for aspartic acid—glycine (The reaction occurs analogously for other susceptible Asx and Glx containing sequences):

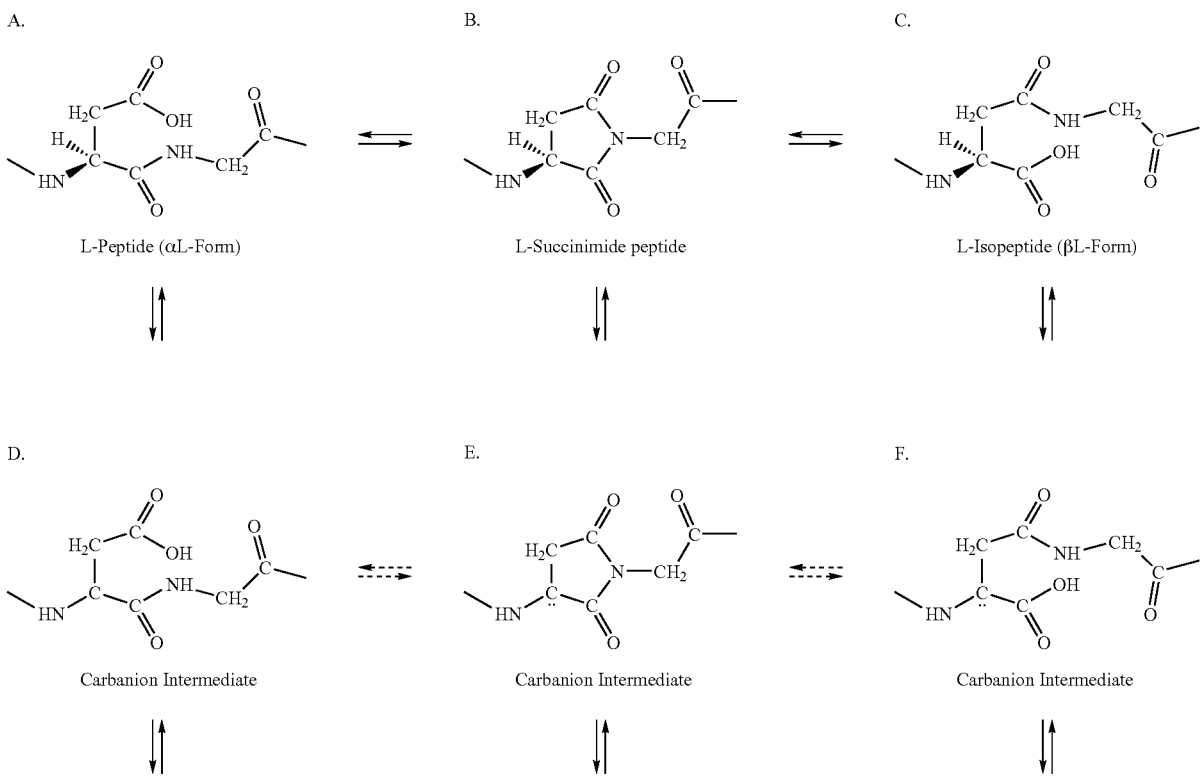

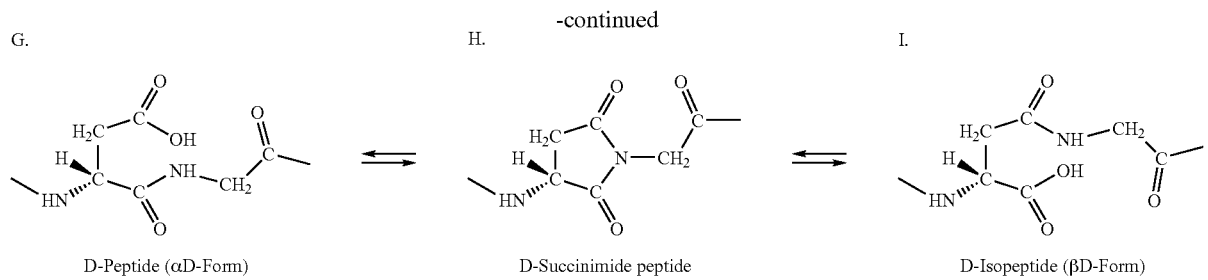

G. D-Peptide (αD-Form)  H. D-Succinimide peptide  I. D-Isopeptide (βD-Form)

The above reaction scheme shows the authentic αL (A) form of the peptide bond as well as the three isomerised and/or optically inverted forms (βL (C), αD (G) and βD (I). The attack by the peptide backbone nitrogen on the side chain carbonyl group of an adjacent aspartyl residue can result in the formation of a succinimide ring, (A→B). The succinimide ring is prone to hydrolysis and optical inversion yielding peptides and iso-peptides in both the D and L configurations. Optical inversion proceeds through a carbanion intermediate (D, E and F) either through direct proton abstraction (A⇌D⇌G or C⇌F⇌I) or via the succinimide pathway (B⇌E⇌H). Throughout the figure the peptide backbone is shown as a bold line.

Cyclic imide formation (and thus isomerisation/optical inversion) can only occur, where the three-dimensional structure surrounding the Asx (asparagine or aspartic acid) or Glx (Glutamine or glutamic acid) has an optimal conformation and sufficient flexibility (Clarke 1987). Isomerisation and optical inversion via the succinimide intermediate as outlined above is a spontaneous reaction occurring with a slow rate under physiological conditions (Geiger & Clarke 1987, Fledelius et al 1997). As for all chemical reactions, increasing temperature can accelerate the reaction speed.

The introduction of such structural changes in a protein or peptide has profound effects on its function, stability and physical and chemical properties. Among other properties, the proteolytic degradation of proteins and peptides containing isomerised and/or optically inverted peptide linkages is significantly reduced compared to proteins and peptides composed exclusively of αL amino acids (Rafferty et al. 1988). Thus, protein fragments containing such modifications are not degraded to the same extent during normal tissue turnover (Van Regenmortel & Muller 1998) and they are much more likely to be present in circulation in measurable concentrations. Furthermore, by measuring proteins, or protein fragments containing isomerised and/or optically inverted peptide linkages, newly synthesized molecules will not contribute to the measurements, and it will thus reflect ongoing degradation processes.

In WO01/38872 (not published at the priority date hereof) we demonstrated that articular cartilage, a tissue with a very slow metabolism, contain proteins which are subject to isomerisation and optical inversion and we demonstrated that measurement of these proteins, or fragments thereof, can provide an index of joint cartilage degradation of diagnostic potential for assessing and monitoring joint diseases such as RA and OA.

We furthermore provided a method which is of general use for identification of markers of catabolic processes in mammalian tissues or organs, based on identification of isomerisation and/or optical inversion sites in extra-cellular matrix proteins and development of diagnostic assays specific for such isomerised and/or optically inverted proteins or protein fragments. By measuring protein fragments containing isomerised or optically inverted residues contributions from anabolic or tissue formation processes is minimized. We have found that isomerised and/or optically inverted fragments of aggrecan as well as collagen type I are found in serum, and that the measurements of such fragments reflect cartilage and bone resorption respectively.

Thus the invention described in WO01/38872 provided a novel approach to identification of biochemical markers of catabolic processes in mammalian tissues or organs, different from previous markers which have been reported as potential markers of i.e. arthritic disease such as YKL-40 (Johansen et al 1993, Johansen et al 1996, Harvey et al 1998), aggrecan (Heinegård et al 1985) or cartilage oligomeric matrix protein (COMP) (Niedhart et al 1997, Saxne et al 1992, Saxne et al 1996). These markers rely on measurement of cartilage proteins in synovial fluid or serum, but as these cartilage proteins can be released during both anabolic and catabolic processes in the cartilage tissue it is not known whether they provide a specific measure of cartilage degradation. By measuring isomerised and/or optically inverted fragments of extra-cellular matrix derived proteins it is ensured that the marker is derived from tissue degradation as the isomerisation process occurs with relatively slow kinetics, and thus only in aged proteins significant isomerisation/optical inversion will have occurred (Radkiewicz et al 1996). Thus, no contribution from tissue formation (anabolic) processes is influencing measures of markers developed from isomerised and/or optically inverted extra-cellular matrix proteins.

The proteins covered by this previous application were aggrecan, cartilage link protein (CLP), cartilage oligomeric protein (COMP) and cartilage intermediate layer protein (CILP).

The present invention now provides in a first aspect a method of assay, comprising measuring in a biological sample the amount or presence of an isomerised and/or optically inverted protein or of one or more isomerised and/or optically inverted fragments from such a protein, wherein said protein is perlecan (SEQ ID NO 1), biglycan (SEQ ID NO 5), decorin (SEQ ID NO 3), fibrillin-1 (SEQ ID NO 10), or protocadherin (SEQ ID NO 8).

The SEQ ID NO's given above are only meant as examples of these proteins, homologous sequences from other mammals also lie within the scope of the present invention.

In a preferred embodiment, the method is based on the competitive binding of a isomerised and/or optically inverted protein or protein fragments produced in vivo or in vitro upon tissue degradation in biological fluids (body fluids or cell culture fluids) and of synthetic peptides essentially derived from such molecules to immunological binding partners.

In second preferred embodiment, the method is carried out using an immunological binding partner specific for a fragment containing an isomerised or optically inverted residue.

For purposes of the present invention, as disclosed and claimed herein, the following terms are defined below:

Antibody: a monoclonal or polyclonal antibody or immunoreactive fragment thereof (i.e. capable of binding the same antigenic determinant), including—but not limited to—Fab, Fab' and F(ab')$_2$ fragments.

*Asx: denotes one of the isomerised or optically inverted forms of asparagine or aspartic acid, which are αD-Asp, αD-Asn, βL-Asp or βD-Asp.

*Glx: denotes one of the isomerised or optically inverted forms of glutamine or glutamic acid, which are αD-Glu, αD-Gln, γL-Glu or γD-Glu.

Isomerised residues: Amino acid residues within a (poly) peptide where said residues are bound to their adjacent residue through an isopeptide bond (e.g. a bond proceeding through the side-chain β or γ-carboxyl group).

Optically inverted residues: D-amino acid residues.

Isomerised (about antigens, peptides, proteins and sequences): Molecules containing isomerised residues (isopeptide bonds).

Optically inverted (about antigens, peptides, proteins and sequences): Molecules containing D-amino acid residues.

Native (about antigens, peptides, proteins and sequences): Antigens/peptides/proteins and sequences composed of L-amino acid residues linked together by normal peptide bonds.

Test kit: A combination of reagents and instructions for use in conducting an assay.

Essentially derived (about structures): Structures with similar antigenicity, i.e. with an ability, above the level of a non-related peptide, to inhibit the binding of any of the mentioned synthetic peptides to an immunological binding partner immunoreactive with said synthetic peptide.

Biological fluid: Body fluids including urine, blood, serum, plasma saliva, sweat and synovial fluid, as well as fluids derived from cells in culture (e.g. supernatants from bone and cartilage cell cultures).

It is contemplated that the method may be used for assaying isopeptide or optically inverted fragments in biological fluids. It can also be used during pre-clinical and clinical testing of drugs to assess the impact of these drugs on metabolism and arthritic disease.

A method according to the invention may preferably determine the amount or presence of at least one of the above mentioned *Asx or *Glx containing proteins or protein fragments in said biological sample, wherein *Asx is αD-Asp, αD-Asn, βL-Asp or βD-Asp and *Glx is αD-Glu, αD-Gln, γL-Glu or γD-Glu.

Such a method may measure the amount of at least one protein or protein fragment containing the perlecan derived amino acid sequence YPVRIESSSASLANGHTL (SEQ ID NO 2) or a fragment thereof containing the E and/or N residue, wherein N denote αL-Asn or an amino acid covered by the term *Asx and E denote αL-Glu or an amino acid covered by the term *Glx (although in view of the requirement that the detected material is isomerised or optically inverted, N will not denote αL-Asn when E denotes αL-Glu).

Such a method may measure the amount of a least one protein or protein fragment containing the decorin derived amino acid sequence IADTNITSIPQGLPPSLTELLDG (SEQ ID NO 4) or a fragment thereof containing the D, E, N and/or Q residue, wherein N denotes αL-Asn or an amino acid covered by the term *Asx, D denotes αL-Asp or an amino acid covered by the term *ASX, E denotes αL-Glu or an amino acid covered by the term *Glx and Q denotes αL-Gln or an amino acid covered by the term *Glx (but for similar reasons not all will be αL).

Such a method may measure the amount of at least one protein or protein fragment containing the biglycan derived amino acid sequence FTLDDGPFMMNDE (SEQ ID NO 6) or a fragment thereof containing the D and/or E residue, wherein D denotes L-Asp or an amino acid covered by the term *Asx and E denotes L-Glu or an amino acid covered by the term *Glx (again not all four will be αL).

Such a method may measure the amount of at least one protein or protein fragment containing the protocadherin derived amino acid sequence YEQFRDLELRVIARDS (SEQ ID NO 8) or a fragment thereof containing the D and/or E residue, wherein D denotes αL-Asp or an amino acid covered by the term *AsX and E denotes αL-Glu or an amino acid covered by the term *Glx (all four will not be αL in the same detected molecule).

Such a method may measure the amount of at least one protein or protein fragment containing the fibrillin-1 derived amino acid sequence YEQFSGGCQDINE (SEQ ID NO 11) or a fragment thereof containing the D, E, N and/or Q residue, wherein N denotes αL-Asn or an amino acid covered by the term *Asx, D denotes αL-Asp or an amino acid covered by the term *Asx, E denotes αL-Glu or an amino acid covered by the term *Glx and Q denotes αL-Gln or an amino acid covered by the term *Glx (again not all will be in the αL form).

Such a method may measure the amount of at least one protein or protein fragment containing the protocadherin derived amino acid sequence YEQFRDLELR (SEQ ID NO 9) or a fragment thereof containing the D and/or E residue, wherein D denotes αL-Asp or an amino acid covered by the term *Asx and E denotes αL-Glu or an amino acid covered by the term *Glx (but not all will be αL).

In an alternative aspect, the invention includes a method of assay, comprising measuring in a sample the amount or presence of an isomerised or optically inverted fragment of a protein, wherein (a) said protein is aggrecan and said fragment contains one of the amino acid sequences: LYPNQTGLPDPLSR (SEQ ID NO 12), SAIIATEQLQAAYEDGFHQC (SEQ ID NO 13), LATTGQLYLAWQAGMDM (SEQ ID NO 14), TGEDFVDIPENFFGV (SEQ ID NO 15), TGEDFVDIPEN (SEQ ID NO 16) or VSLPNYPAIPSDATLEVQSLRSNDSGVYR (SEQ ID NO 17) or a fragment thereof containing the D, E, N and/or Q residue, wherein N denotes αL-Asn or an amino acid covered by the term *Asx, D denotes αL-Asp or an amino acid covered by the term *Asx, E denotes αL-Glu or an amino acid covered by the term *Glx and Q denotes αL-Gln or an amino acid covered by the term *Glx.;

(b) said protein is type II collagen and said fragment contains the amino acid sequence EGSXGADGPXGRDG (SEQ ID NO 18) or a fragment thereof containing the D and/or E residue, wherein D denotes αL-Asp or an amino acid covered by the term *Asx and E denotes αL-Glu or an amino acid covered by the term *Glx;

(c) said protein is COMP and said fragment contains the amino acid sequence AQEDSDH (SEQ ID NO 19) or a fragment thereof containing the D, E and/or Q residue, wherein D denotes αL-Asp or an amino acid covered by the term *Asx, E denotes αL-Glu or an amino acid covered by the term *Glx and Q denotes αL-Gln or an amino acid covered by the term *Glx.; or (d) said protein is CILP and said fragment contains the amino acid sequence LLTQTDSDGR (SEQ ID NO 20) or a fragment thereof containing the D and/or Q residue, wherein D denotes αL-Asp or an amino acid covered by the term *Asx and Q denotes αL-Gln or an amino acid covered by the term *Glx.

Fragments for detection as described above may preferably contain at least 4 amino acids, more preferably at least 8 amino acids.

In all of the above sequences, the amino acids marked by bold type face are of particular interest as sites of isomerisation or optical inversion. Only one of these sites need to be in an isomerised or optically inverted state in order to carry out the present invention.

The measurement performed in the methods of the present invention maybe carried out using an immunological binding partner which specifically binds an amino acid sequence comprising *Asx or *Glx.

Said immunological binding partner may be an antibody raised against a synthetic peptide having an amino acid sequence comprising *Asx or *Glx, or fragment of such an antibody having immunological binding specificity.

Preferably, said amino acid sequence corresponds to a characteristic sequence of a protein or fragment thereof covered by the present invention, with *Asx or *Glx substituting αL-Asp, -Asn, -Gln, or -Glu in said protein sequence.

Said measurement may provide an index of cartilage turnover relevant for conditions and diseases affecting joint tissue turnover.

Optionally the method further comprises carrying out a measurement of a second index of joint disease and determining the value of a parameter mathematically combining said two indices.

Thus the invention includes the use of ratios between measurements for monitoring a pathological situation or therapeutic intervention in a mammal, applying two or more assays specific for isomerised and/or optically inverted proteins or protein fragments from an extracellular matrix protein as described in the above.

The ratios can be generated from any such marker consisting of an isomerised and/or optically inverted protein or protein fragment from an extracellular matrix protein measured by the assays as described and other markers of tissue metabolism and/or tissue function for monitoring a pathological situation or therapeutic intervention in a mammal.

The invention includes the use of an isomerised and/or optically inverted protein or of one or more isomerised and/or optically inverted fragments from such a protein in an in vitro method of assay for the diagnosis or the assessment of the severity of OA or RA, comprising measuring in a biological sample the amount or presence of an isomerised and/or optically inverted protein or of one or more isomerised and/or optically inverted fragments from such a protein, wherein said protein is perlecan, biglycan, decorin, fibrillin-1, or protocadherin.

The invention include the use of an immunological binding partner which specifically binds an amino acid sequence comprising *Asx or *Glx flanked by amino acid residues of perlecan, biglycan, decorin, fibrillin-1, or protocadherin in an in vitro method for use in the diagnosis or the assessment of the severity of OA or RA.

In another aspect, the invention provides an immunological binding partner which specifically binds an amino acid sequence comprising *Asx or *Glx flanked by amino acid residues of perlecan, biglycan, decorin, fibrillin-1 or protocadherin.

The immunological binding partner may specifically bind a sequence set out above.

The invention includes a cell line producing a monoclonal antibody which is an immunological binding partner described herein.

The invention further includes a peptide of up to 20 (e.g. 4 to 20 or 8 to 20) amino acids in length containing *Asx or *Glx flanked by amino acid residues of perlecan, biglycan, decorin, fibrillin-1, or protocadherin.

The peptides described maybe used in assays providing therapeutic information for treating a pathological condition in a mammal.

The invention includes a method of immunoassay in which a biological sample is contacted with an immunological binding agent in the presence of a peptide, as described, acting as a competition agent for binding to said immunological binding agent.

In a further aspect there is provided a test kit comprising (a) an immunological binding partner as described herein or (b) a peptide as described herein. Versions of the test kit combine (a) and (b), optionally in combination with one or more apparatus in which to perform an immunoassay, an antibody-enzyme conjugate, a substrate for an enzyme component of an antibody-enzyme conjugate, an enzyme-substrate reaction stopping composition, or a wash solution, a carrier bound to said binding partner or a detectable label bound to said binding partner.

The invention also includes cell lines (e.g. hybridomas) that produce monoclonal antibodies immunoreactive with the above-mentioned proteins, fragments thereof or synthetic peptides. The invention further includes monoclonal antibodies produced by the fused cell hybrids, and those antibodies (as well as binding fragments thereof, e.g. Fab) coupled to a detectable marker. Examples of detectable markers include, but are not limited to, enzymes, chromophores, fluorophores, co-enzymes, enzyme inhibitors, chemiluminescent materials, paramagnetic metals, spin labels and radioisotopes.

The methods of the invention typically involve quantitating in a biological fluid the concentration of particular isopeptide fragments derived from tissue degradation. In a representative assay, isopeptide fragments in the biological fluid and a synthetic peptide immobilized on a solid support are contacted with an immunological binding partner, which is immunoreactive with the synthetic peptide as well as the isopeptide fragments, thereby generating a competition assay.

The biological fluid may be used as it is, or it may be purified prior to the contacting step. This purification step may be accomplished using a number of standard procedures, including but not limited to, cartridge adsorption and elution, molecular sieve chromatography, dialysis, ion exchange, alumina chromatography, hydroxyapatite chromatography, and combinations thereof.

The invention also includes test kits useful for quantifying in a body fluid (or cell supernatant) the amount of isopeptide fragments derived from the degradation of tissue. The kits comprise at least one immunological binding partner, e.g. a monoclonal or polyclonal antibody specific for a peptide derived from the degradation of a relevant protein. If desired, the immunological binding partner of the test kit may be coupled to detectable markers such as the ones described above. Generally speaking, the immunological binding partner is therefore also useful as a diagnostic agent.

Various non-immunological methods of assay may also be employed for analysis and identification of isoaspartyl, D-aspartyl and D-isoaspartyl within proteins or peptides.

The presence isoapartyl (D-aspartyl and D-isoaspartyl) within a peptide or protein may be determined by methods well known in the art. These methods include the use of 1) chromatographic methods, 2) electrophoretic techniques, 3) enzymatic methods 4) immunological methods, 5) chemical methods or combinations thereof. A review of current methods for detection and quantitation of isoaspartate is provided in by Aswad and Guzzetta (Aswad and Guzzetta, 1995).

Chromatographic methods maybe used, such as reversed phase HPLC (Cloos and Fledelius 2000) and hydrophobic interaction chromatography (Di Donato et al 1993). The structural alterations associated with isoaspartyl (D-aspartyl and D-isoaspartyl) formation can produce significant changes in the retention of peptides in various chromatographic methods.

Electrophoretic techniques as native gel-electrophoresis (Potter et al 1993), capillary electrophoresis (Stevenson et al 1993) and thin-layer electrophoresis (Aswad et at 1987) can be used to separate and may be used as means to identify such changes.

Enzymatic methods, including the use of the IAMT enzyme (EC 2.1.1.77) or of specific proteases specifically cleaving at the N or C of isoaspartyl residues may be used to identify such changes.

The enzyme IsoAspartyl (D-aspartyl) MethylTransferase (IAMT), EC 2.1.1.77 provides a method for selectively labelling isoaspartyl (D-aspartyl) sites with-methyl groups. This enzyme has the ability to recognise and methylate atypical isoAsp and D-Asp residues. By employing a radioactively labelled methyl-donor ($^3$H or 14C-methyl), isomerised (or optically inverted) proteins or peptides incubated with this enzyme will be radioactively labelled, and labelling of the protein can be detected by measuring the incorporated radioactivity. A kit (IsoQuant™), based on this principle is commercially available.

Alternative methods for IAMT-dependent isoAsp analysis have recently been described. Thus isoAsp formation has been detected utilizing HPLC in conjunction with UV-detection to monitor production of S-adenosyl-L-Homocysteine (Aswad et al 2000).

Proteases that selectively cleave at the N or C of isoaspartyl (D-aspartyl or D-isoaspartyl) may be useful for isoAsp analysis. As an example of this the Carboxypeptidase Y recognises L-isoaspartyl sites as if they were C-terminal amino acids and thereby acts as an "endoproteinase iso-asp-N" (Johnson and Aswad 1990). This action combined with normal CP-Y sequential clipping at the real terminus, can result in the production isoaspartyl dipeptides that can be charactized by amino acid analysis techniques. Such an approach may be useful in tracking down sites of isoAspartyl formation in proteins or peptides.

The Edman degradation is an important method for determining the location of an Asx alteration in a peptide, especially when used in conjunction with a complementary technique such as mass spectrometry or enzymatic methylation of isoaspartate. It has long been known that the presence of an isopeptides bond causes blockage of the Edman degradation because the extra carbon(s) in the backbone of isopeptides prevent cyclization of the phenylthiocarbamyl peptide to form the anilinothiazolone derivative (Smyth et al 1963). Thus a sequencing block at Asx (or Glx) sites provides powerful, albeit indirect, evidence for the presence of an isopeptide bond.

Matsuo and Narita have described a method based on Oxasolone Formation for selectively labelling the C-terminal α-carboxylamino acid of a peptide (Matsuo and Narita 1975). This method can be used to label internal isoaspartyl residues since they contain a free α-carboxyl. As an example of this Di Donato and colleagues have used 3H-labelling to confirm the presence of isoaspartate in peptides derived from bovine seminal ribonuclease and pancreatic ribonuclease.

Alkaline hydroxylamine has been used to cleave proteins mainly at Asn-Gly bonds The relative selectivity of this method is due to the propensity of Asn-Gly to be rapidly deamidated via the succinimide pathway at alkaline pH.

BRIEF DESCRIPTION OF THE DRAWINGS

The invention will be further described and illustrated by the following examples, in which reference is made to the accompanying drawings, in which.

EXAMPLE 1

Purification of Isomerised and/or Optically Inverted Protein Fragments Derived from Cartilage, and Identification of Specific Isomerisation and/or Optical Inversion Sites in Cartilage Proteins Scheme I:
Flow-sheet for the Characterisation of isoAsp in Cartilage proteins

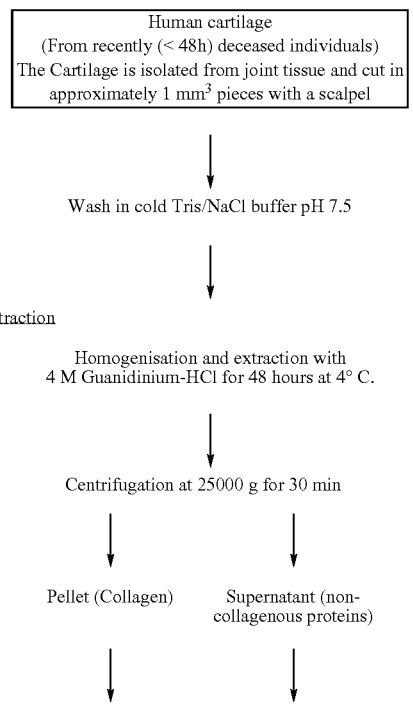

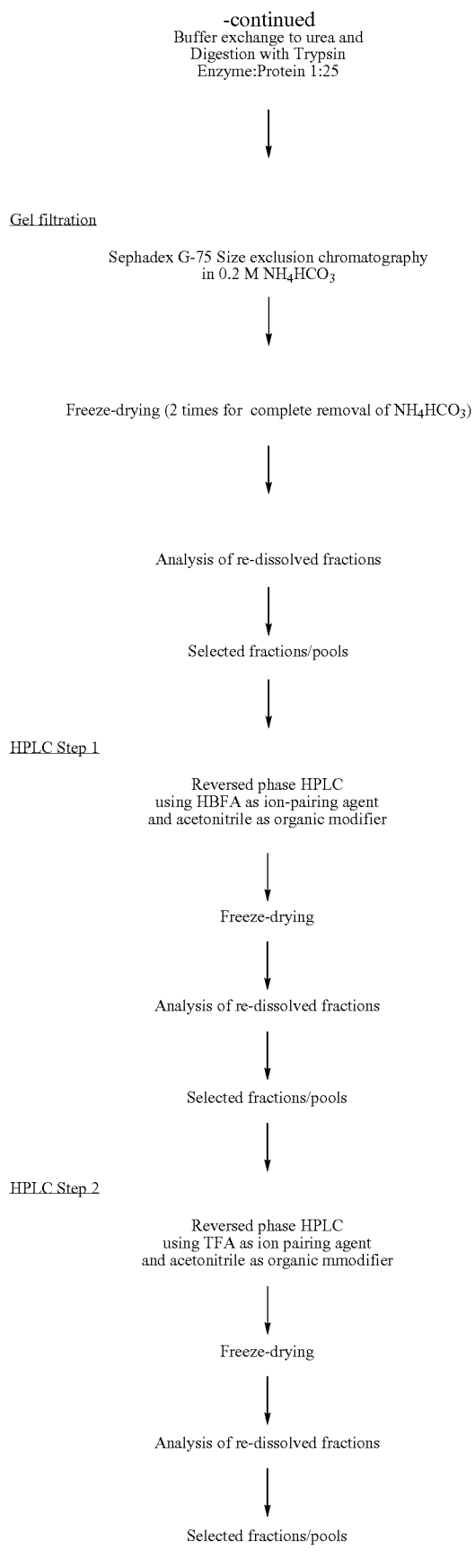

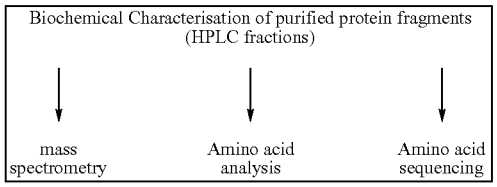

Figure 1:
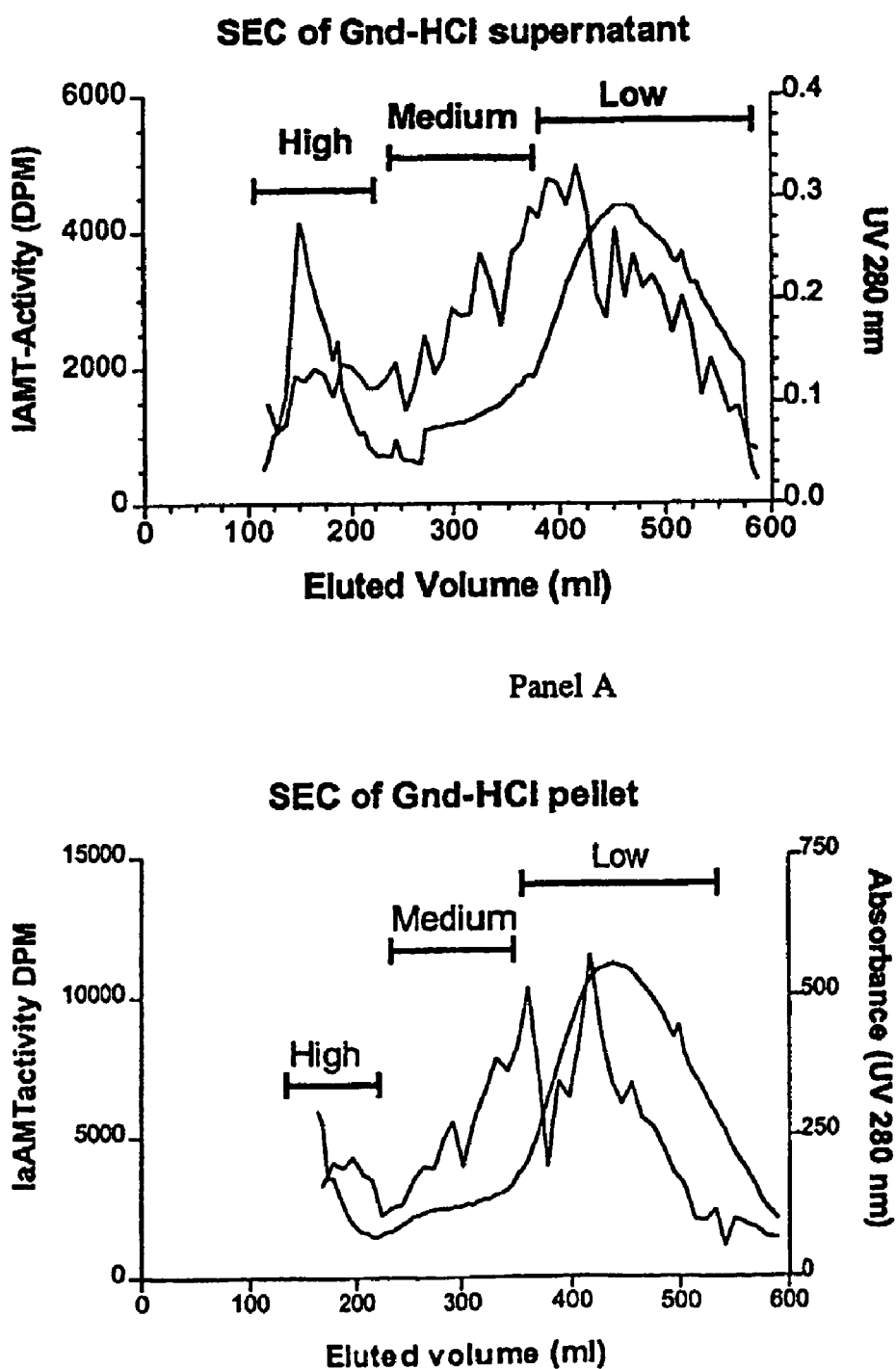
FIG. 1 shows in panels A and B the results of size exclusion chromatography of trypsin digested extracted (soluble fraction) and non-extractable (pellet) proteins from cartilage as described in Example 1.

Cartilage samples from two deceased human subjects (each approximately 20 mg wet-weight) (obtained from the department of forensic pathology of Copenhagen university hospital), were homogenized (with an ultra-turax homogeniser) and treated with 4 M guanidinium hydrochloride (Gnd-HCl) for 48 h at 4° C. The extraction mixture was subsequently centrifuged at 27,000×g and the supernatant and pellet separated. Gnd-HCl was removed by extensive dialysis against Milli-Q water (MWCO=10 kDa, spectropor dialysis membranes) and lyophilised. Aliquots of the "Pellet" and "supernatants" were subsequently digested with trypsin (enzyme:substrate 1:25). Tryptic digests (of Gnd-HCl pellet and Gnd-HCl supernatant from extraction of cartilage) were subjected to size-exclusion chromatography (SEC) on a 500 ml Sephadex G-75 column. Eluents were collected in fractions and measured in relevant assays (IAMT, CartiLaps and AG1-ELISA). The eluate from the size exclusion column was analysed by OD214 nm, and after lyophilization and re-solubilization in phosphate buffered saline (PBS) in an enzyme assay using IAMT for detection of isomerised aspartate residues. IAMT-reactivity was found primarily in the medium and low-molecular weight fractions. No CartiLaps activity was found in eluents, and AG1-1 activity was almost exclusively restricted to the medium molecular weight fractions. Results are shown in FIG. 1.

Figure 2:
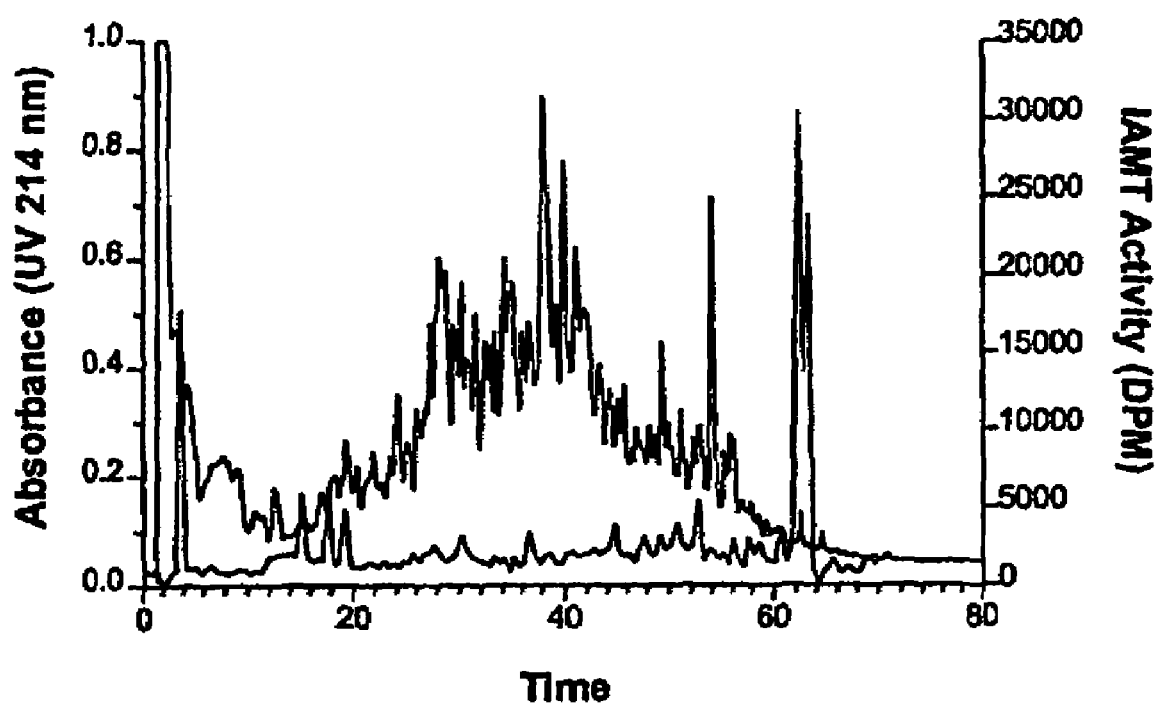
FIG. 2 shows the results of reverse phase HPLC fractionation of low molecular weight fraction from tryptic digest of Gnd-HCl pellet, with typing of isoAsp/DAsp sites, as described in Example 1.

Low molecular fractions were pooled, lyophilised and further separated by reversed phase HPLC. Low molecular fractions from SEC of tryptic digests (of Gnd-HCl supernatant and Gnd-HCl pellet, FIG. 1) were separated by R.P. HPLC. Eluents were collected in fractions and measured in the IAMT assay. Several IAMT-reactive fractions were found, these were further purified by R.P.HPLC and subsequently subjected to amino acid sequencing and mass spectrometry to identify isoAsp (D-Asp)-containing sequences. Results as shown in FIG. 2.

IAMT-positive fractions from the first HPLC separation were isolated and subjected to a second R.P. HPLC run, eluents were collected in fractions and measured in the IAMT assay. Purified fragments were subjected to mass spectrometry and amino acid sequencing for identification of isomerisation/optical inversion sites. The following cartilage protein fragments were identified: 5 in Aggrecan, 1 in Decorin, 1 in Biglycan, 1 in perlecan, 1 in protocadherin, 1 in Fibrillin and 1 in collagen type II.

Aggrecan site 1 (Pool 3 Frac 7, 8): LYPNOTGLPDPLSR (SEQ ID NO 12)

Aggrecan site 2 (Pool 2 Frac 82): SAIIATEQLQAAYEDGFHQC (SEQ ID NO 13)

Aggrecan site 3 (Frac 3.88 pool 1): LATTGOLYLAWQAGMDM (SEQ ID NO 14)

Aggrecan site 4 (Pool 9 and 10, trial 105): TGEDFVDIPENFFGV (SEQ ID NO 15)

Aggrecan site 5 (Pool 5, Frac 28): VSLPNYPAIPSDATLEVQSLRSNDS GVYR (SEQ ID NO 17)

Decorin (Trial 100, Frac 112): <u>IADTNITSIPQGLPPSLTELLDG</u> (SEQ ID NO 4)

Perlecan (Frac 3.75, pool 2): <u>YPVRIESSSASLANGHTL</u> (SEQ ID NO 2)

Protocadherin gamma A11 (Frac 3.8, pool 2): <u>YEOFRDLELR</u> (SEQ ID NO 9)

Fibrillin-1 (Frac 3.8, pool 2): <u>YEOFSGGCQDINE</u> (SEQ ID NO 11)

Biglycan (Trial 91, Frac 4.36.2): <u>FTLDDGPFMMNDE</u> (SEQ ID NO 6)

Collagen type II (Trial 91, Frac 4.36.1): <u>EGSXGADGPXGRDG</u> (SEQ ID NO 18)

The amino acid residues given in bold denotes isomerisation and optical inversion prone Aspartate and asparagine residues. The underlined residues denote the amino acids identified by sequencing the rest are extrapolated from the fragment mass identified by mass spectroscopy.

EXAMPLE 2

Development of Antibodies Specific for Isomerised and/or Optically Inverted Proteins or Protein Fragments and Generation of Immunoassays Specific for Isomerised and/or Optically Inverted Proteins or Protein Fragments Immunogen for generation of a specific antiserum can be generated by two procedures. The authentic protein or fragments of the protein from an extra-cellular tissue can be purified by conventional chromatographic procedures as outlined in example 1. The isomerisation degree of the purified protein or protein fragments can be determined by use of the IAMT assay, and thus proteins or protein fragments containing a high isomerisation degree (i.e. more than 0.5 mol isoAsp/mol protein or protein fragment) can be used for the immunizations. Alternatively synthetic peptides representing the isomerisation sites identified in a given extra-cellular matrix protein can be synthesized by conventional peptide synthesis methods (please refer to 'Stewart, J. Young, J., "Solid phase peptide synthesis" Pierce Chemical Company, Rockford, Ill., USA 1984' and 'Atherton, E., Sheppard, R. C., "Solid phase peptide synthesis: a practical approach", IRL Press, Oxford, 1989'). Synthetic peptide can be made containing an isomerised and/or racemised Asx or Glx residue and a suitable number of amino acid residues on both sides of the residue (i.e. 1-15 amino acid residues, preferably 2-6) derived from the primary sequence of the given isomerisation prone extra-cellular matrix protein.

A synthetic peptide or protein or protein fragment ('β-antigen') containing an isomerised and/or racemised Asx or Glx residue can be used for immunisation of rabbits and generation of a specific antiserum as described in the following. The β-antigen is conjugated to a carrier protein by the use of the covalent cross-linking agent 1-ethyl-3-[3-dimethylaminopropyl]carbodi-imide hydrocloride (CDI) (Pierce, Rockford, Ill., USA). A conjugate of the β-antigen peptide is prepared essentially according to: Greg T. Hermanson, 'Bioconjugate techniques' 1996, Academic press, San Diego, USA. Briefly described the CDI conjugates are prepared as follows: One-hundred mg of Thyroglobulin is dissolved in 10 ml to a concentration of 10 mg/ml in 0.05 M MES, 0.5 M NaCl, pH 6.0. One-hundred µl of the two following reagents (to a final concentration of 4 mM CDI, corresponding to approximately 100 fold molar excess of CDI to thyroglobulin, and 10 mM NHS) is added, and the solution is left to mix 15 min at room temperature (18-22° C.). CDI: 0.4 M CDI stock: 76.7 mg in 1 ml water prepared immediately prior to use. NHS: 1 M sulfo-NHS stock: 217.1 mg in 1 ml water prepared immediately prior to use.

Excess cross-linking reactants (CDI) is removed by gel-filtration on four NAP25 de-salting columns (Amersham Pharmacia Biotech, Uppsala, Sweden) into 10 mM Na-Phosphate pH 9.0. The de-salted activated thyroglobulin is pooled and divided into 6 portions of 2 ml. Immediately following the gel-filtration peptide solutions: 2 ml 4 mg/ml in 0.1 M Na-Phosphate pH 9.0 is added to each vial. A control conjugation is carried out with an irrelevant peptide. The coupling reaction is allowed to proceed for two hours at room temperature.

The β-antigen conjugates are changes into PBS (pH 7.4) by gel-filtration on Sephadex G25 columns (Amersham Pharmacia Biotech, Uppsala, Sweden), and the concentration is adjusted to 2 mg/ml in PBS.

Rabbits (strain SSC:CPH), are immunised sub-cutaneously with 1 ml 0.25 mg/ml of the vaccinein phosphate buffered saline (PBS), containing 50% Freunds incomplete adjuvant. Rabbits are boosted after initial immunisations at two weeks intervals. After the three first boosts, subsequent booster immunisations are performed at one month intervals. Pre-immune bleed is collected before immunisation and test bleeds are collected one week after the $2^{nd}$ immunisation to monitor serum antibody levels. Bleeds are subsequently collected one week after the $5^{th}$ and $6^{th}$ immunisation.

The specificity of the rabbit bleed are tested on a micro titre plates (MTP) coated with a β-antigen conjugate prepared with the same β-antigen as used for the immunization. The β-antigen is conjugated to bovine serum albumin (BSA) by us of the bi-functional cross-linker bis[sulfosuccinimidyl] suberate ($BS^3$). This crosslinking reagent is obtained from Pierce (Rockford, Ill., USA) and the conjugation is prepared essentially as disclosed by the manufacturer. Briefly described the following procedure. Peptide stocks (β-antigen) are prepared in freshly filtered PBS to 2 mg/ml. The carrier protein (BSA) is prepared in 3 mg/ml concentration in PBS (approximately 50 fold molar excess of peptide). 200 µl of carrier protein is mixed with 200 µl peptide solution in an Eppendorf tube. BS3 (Bis-(sulfosuccinimidyl) suberate) 6 mg/ml is prepared in 5 mM sodium-citrate pH 5.0 (25 fold molar excess of cross-linker compared to carrier protein). 50 µl of the cross-linker is added to the carrier and peptide solution, which is vortexed and placed on a mixer at room temperature for 30 min. 50 µl 0.25 M glycine pH 7.5 is added to the solutions. The incubation is continued for 15 min., Whereafter the conjugates are desalted on NAP5 column and protein concentrations are determined by the Bradford or Loewry methods. MTP are coated with 10 ng/ml of the BSA-$BS^3$-β-antigen conjugate and used for screening of serum from the immunized rabbits. The rabbit antiserum is diluted in PBS containing 1% BSA and 0.1% Tween in a suitable dilution for obtaining an appropriate ELISA signal (a suitable signal is between 1 and 3 absorbency units and a suitable dilution will typically be in the range between 1000 fold dilution and 100,000 fold dilution). The bound antibody in this competitive assay format was detected by use of a secondary peroxidase conjugated goat anti rabbit antibody and a chromogenic peroxidase substrate.

EXAMPLE 3

Generation of Antibodies Specific for an Isomerised Fragment of Cartilage Oligomeric Matrix Protein (β-COMP) and Development of a β-COMP Specific Immunoassay Peptide Conjugation A synthetic peptide derived from human cartilage oligomeric matrix protein (COMP) containing an isomerised Asp residue within the sequence AQED$_β$SDH('β-COMP') SEQ ID NO: 21 was used for immunisation of mice and generation of a specific antiserum as described in the following. The β-COMP peptide was conjugated to a carrier protein by the use of the covalent cross-linking agent 1-ethyl-3-[3-dimethylaminopropyl]carbodi-imide hydrocloride (CDI) (Pierce, Rockford, Ill, USA). The β-COMP conjugate was prepared essentially according to: Greg T. Hermanson, 'Bioconjugate techniques' 1996, Academic press, San Diego, USA. Briefly described the CDI conjugates were prepared as follows: One-hundred mg of thyroglobulin was dissolved to a concentration of 10 mg/ml in 0.05 M MES, 0.5 M NaCl, pH 6.0 in a total volume of 10 ml. One-hundred µl containing a final concentration of 4 mM CDI and 10 mM NHS was added to the thyroglobulin solution. The solution was left to mix 15 mm at room temperature (18-22°C). CDI: 0.4 M CDI stock: 76.7 mg in 1 ml water prepared immediately prior to use. N-hydroxysulfosuccinimide (NHS from Pierce, Rockford, Ill., USA): 1 M NHS stock: 217.1 mg in 1 ml water prepared immediately prior to use.

Excess cross-linking reactants (CDI) were removed by gel-filtration on four NAP25 de-salting columns (Amersham Pharmacia Biotech, Uppsala, Sweden) into 10 mM Na-Phosphate pH 9.0. The de-salted activated thyroglobulin was pooled and divided into 6 portions of 2 ml. Immediately following the gel-filtration 2 ml β-COMP peptide solution of 4 mg/ml in 0.1 M Na-Phosphate pH 9.0 was added to each vial. A control conjugation was carried out with an irrelevant peptide. The coupling reaction was allowed to proceed for two hours at room temperature.

The β-COMP conjugates were changed into phosphate buffered saline (PBS) (pH 7.4) by gel-filtration on Sephadex G25 columns (Amersham Pharmacia Biotech, Uppsala, Sweden), and the concentration was adjusted to 0.5 mg/ml in PBS.

Immunisation

Mice (strain Balb/C-J) were immunised sub-cutaneously with 0.2 ml 0.25 mg/ml β-COMP conjugate in PBS, containing 50% Freunds incomplete adjuvant. Mice were boosted after initial immunisations at two weeks intervals. Pre-immune bleeds were collected before immunisation and test bleeds were collected one week after the 2$^{nd}$ immunisation and after subsequent booster immunisations to monitor serum antibody levels.

Specificity

Figure 3:
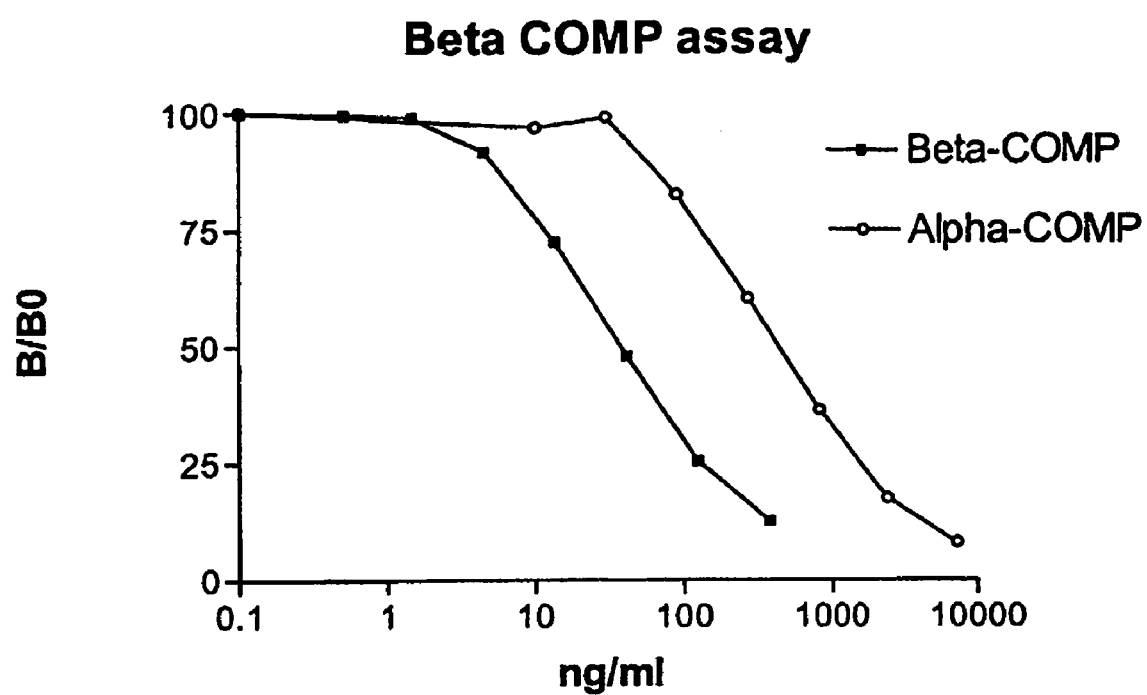
FIG. 3 shows results from the competitive β-COMP assay of example 3. Peptide standard curves with 20 μl/well of the isomerised (β) form and the non-isomerised (α) form of COMP peptide. 50% inhibition of the signal (Bo) was obtained with 38 ng/ml β-COMP peptide and 435 ng/ml α-COMP peptide.

The specificity of the mouse bleeds were tested on streptavidin micro titer plates (Micro-coat, Munich, Germany) coated with 10 ng/ml biotinylated-β-COMP. The β-COMP biotinylation was prepared using standard conjugation techniques with a succinimide activated form of biotin, according to the manufactures instructions (Pierce, Rockford, USA). The mouse sera were diluted in PBS containing 1% BSA and 0.1% Tween (PBS-BTB) to a dilution giving an appropriate ELISA signal (OD-value of ≈2). Specificity for the isomerised form of the COMP peptide was tested by competition with both the isomerised (β) and the non-isomersied (α) form of the COMP peptide. The mouse serum that showed the highest degree of specificity for β-COMP was used for development of a competitive assay for measurement of β-COMP in serum samples (FIG. 3).

Briefly the assay was set-up as follows; streptavidin pre-coated micro titer plates (MicroCoat, Munich, Germany) were incubated with 100 µl/well of 0.5 ng/ml biotinylated-β-COMP in PBS-BTB at 20° C. for 30 minutes at a shaking table. The plates were washed 5 times in PBS with 0.1% Tween 20 (PBS-T), followed by overnight incubation at 4° C. with 100 µl/well mouse-anti-β-COMP sera diluted 1:8000 in PBS-BTB and 20 µl/well of standards containing 0.5, 1.5, 4.5, 13.5, 41.5, 125 and 375 ng/ml β-COMP peptide in PBS-BTB or 20 µl/well of serum samples from patients with osteoarthritis or healthy individuals. The plates were washed five times in PBS-T. 100 µl secondary peroxidase conjugated sheep-anti-mouse IgG antibody (Jackson Immuno Research, Pennsylvania, USA) diluted 1:2000 in PBS-BTB was added to each well and incubated for 60 minutes at 20° C. on a shaking table. After washing five times in PBS-T the amount of bound peroxidase conjugated antibody was detected by 15 minutes incubation with 100 µl/well of a chromogenic peroxidase substrate (3,3',5,5'-tetramethyl-benzidine (TMB) from KemEnTek, Copenhagen, Denmark) on a shaking table. The reaction was stopped with 100 µl/well of 0.18 M H$_2$SO$_4$ and micro titer plates were read at 450/650 nm.

Figure 4:
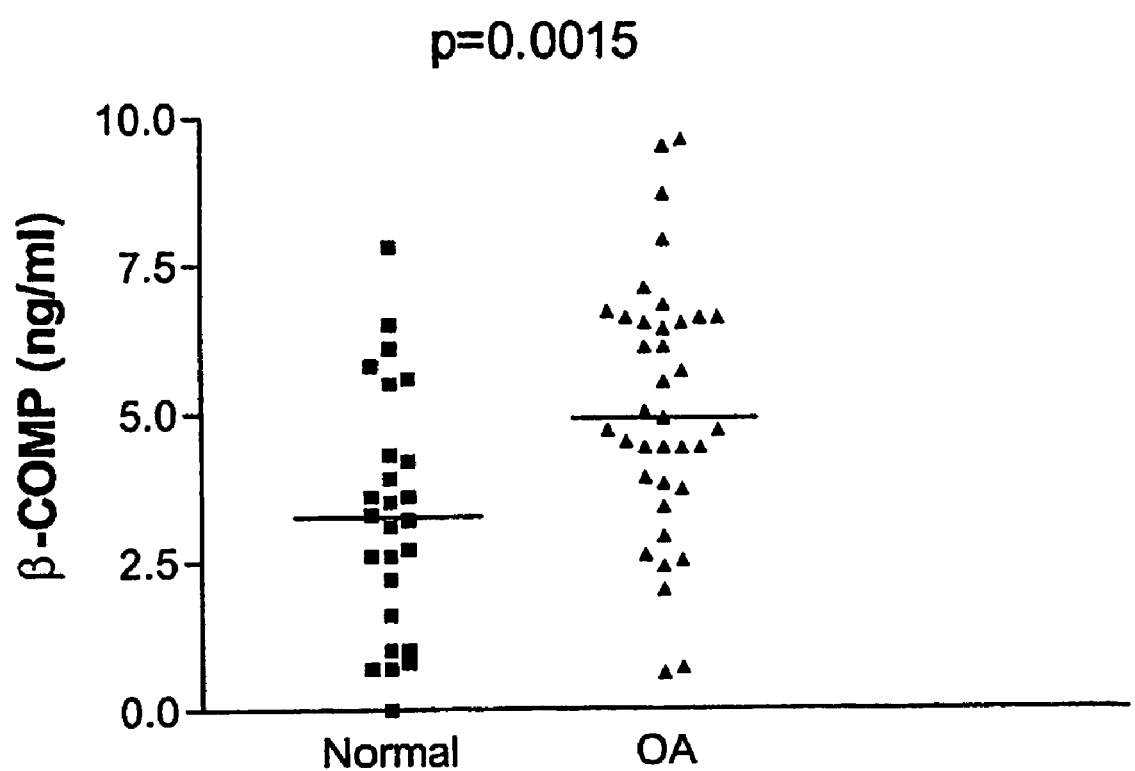
FIG. 4 shows the results of β-COMP measurements in serum from 26 healthy individuals and 36 Osteo-arthritis patients. The samples were measured in the β-COMP ELISA (example 3). The significance of the difference between the groups was calculated by non-parametric T-Test to p=0.0015.

The amount of β-COMP peptide in serum samples from healthy individuals, patients with osteo-arthritis (OA) (FIG. 4) and rheumatoid arthritis (RA) (not shown) were calculated from the β-COMP peptide standard curve.

Conclusion

It is apparent that circulating levels of β-COMP fragments can be measured in normal adult individuals as well as in patients with arthritis. In the QA and RA patients the levels of β-COMP is significantly elevated compared to the healthy controls. This demonstrates that the β-COMP marker measured in a specific immunoassay employing a polyclonal antiserum specific for the human COMP derived sequence AQED$_β$SDH (SEQ ID NO: 21) reflects the elevated cartilage turnover associated with the pathologic joint tissue processes in RA and OA.

REFERENCES

1. Adams J C, Tucker R P. (2000). The thrombospondin type 1 repeat (TSR) super-family: diverse proteins with related roles in neuronal development. Dev Dyn. 218: 280-299
2. Clarke A G et al. Serum cartilage oligomeric matrix protein reflects osteoarthritis presence and severity: the Johnston County. Osteoarthritis Project. Arthritis Rheum. 1999, 42, 2356-2364
3. Clarke S (1987). Propensity for Spontaneous Succinimide Formation from Aspartyl and Asparginyl Residues in Cellular Proteins. Int. J. Peptide Protein Res. 30: 808-821.
4. Costell M, Gustafsson E, Aszodi A, Mörgelin M, Bloch W, Hunziker E, Addicks K, Timpl R, Fassler R. (1999). Perlecan maintains the integrity of cartilage and some basement membranes. J. Cell Biol. 147: 1109-1122.

5. Dodge G R, Hawkins D, Boesler E, Sakai L, Jimenez S A. Production of cartilage oligomeric matrix protein (COMP) by cultured human dermal and synovial fibroblasts. Osteoarthritis Cartilage, 1998, 6, 435-440
6. Eyre D R (1991) The collagens of articular cartilage *Semin. Arthritis Rheum.* 21 (suppl. 2): 2-11.
7. Flannerly C R et al. (1992). Identification of a stromelysin cleavage site within the interglobular repeats of human aggrecan. Evidence for proteolysis at this site in vivo in human articular cartilage. *J. Biol. Chem.* 267: 1008-1014.
8. Fledelius C, Johnsen A H, Cloos P A C, Bonde M, Qvist P. 1997. Characterization of urinary degradation products derived from type I collagen. Identification of a β-isomerized Asp-Gly sequence within the C-telopeptide (α1) region. J. Biol. Chem.; 275: 9755-9763.
9. Ganu V, Goldberg R, Peppard J, Rediske J, Melton R, Hu S I, Wang W, Duvander C, Heinegard D. Inhibition of interleukin-1alpha-induced cartilage oligomeric matrix protein degradation in bovine articular cartilage by matrix metalloproteinase inhibitors: potential role for matrix metalloproteinases in the generation of cartilage oligomeric matrix protein fragments in arthritic synovial fluid. Arthritis Rheum. 1998, 41, 2143-2151.
10. Geiger T and Clarke S (1987). De-amidation, Isomerization and Racemization at Asparginyl and Aspartyl Residues in Peptides. J. Biol. Chem. 262(2): 785-794.
11. Hardingham T E and Fosang A J (1992) FASEB J 6: 861-870.
12. Hardingham T E and Muir H (1972) The specific interaction of hyaluronic acid with cartilage proteoglycans. *Biochem Biophys Acta* 279:401-405.
13. Harvey S, Weisman M, O'Dell J, Scott T, Krusemeier M, Visor J, Swindlehurst C. 1998 Chondrex: new marker of joint disease. Clin. Chem. 44: 509-516.
14. Heinegård D, Inerot S, Wieslander J, and Lindblad G et al. (1985) A Method for the quantification of cartilage proteoglycan structures liberated to the synovial fluid during developing degenerative joint disease *Scand J Clin Lab Invest* 45:421-427.
15. Heinegård D, Lorenzo P and Saxne T (1999) Noncollagenous Proteins; Glycoproteins and related proteins. In Seibel M J, Robins S P and Bilezikian J P (Eds.) *Dynamics of Bone and Cartilage Metabolism*. Academic Press, New York, pp.:59-69.
16. Greg T. Hermanson, 'Bioconjugate techniques' 1996, Academic press, San Diego, USA
17. Inerot S, and Heinegård D (1982). Articular cartilage proteoglycans in aging and osteoarthritis. In Horowitz MI (ed.) *Glycoconjugates Vol. IV*, Academic Press, New York: pp. 335-355.
18. Johansen J S, Jensen H S, Price P A. (1993). A new biochemical marker for joint injury. Analysis of YKL-40 in serum and synovial fluid. Br. J. Rheumatol. 32: 949-955.
19. Johansen J S, Hvolris J, Hansen M, Backer V, Lorentzen I, Price P A (1996). Serum YKL-40 levels in healthy children and adults. Comparison with serum and synovial fluid levels of YKL-40 in patients with osteoarthritis or trauma of the knee joint. Br. J. Rheumatol. 35:553-559.
20. Kudson C B, Knudson W (2001) Cartilage proteoglycans. Semin. Cell Dev. Biol. 12: 69-78
21. Lorenzo P, Bayliss, M T, and Heinegård D. (1998a). A Novel Cartilage Protein (CILP) Present in the Mid-zone of Human articular cartilage Increases with age. J. Biol. Chem. 273(36):23463-23468.
22. Lorenzo, P., Neame, P., Sommarin, Y., and Heinegård D. (1998b). Cloning and Deduced Amino Acid Sequence of a Novel Cartilage Protein (CILP) Identifies a Proform Including a Nucleotide Pyrophosphohydrolase. J. Biol. Chem 273(36): 23469-23475.
23. Niedhart M, Hauser N, Paulsson M, DiCesare P E, Michel B A, Hauselmann H J (1997). Small fragments of cartilage oligomeric matrix protein in synovial fluid and serum as markers for cartilage degradation. *Br. J. Rheumatol.* 36: 1151-1160.
24. Poole A R, Dieppe P. 1994 Biological markers in rheumatoid arthritis. Sem. Arthr. Rheum. 23: 17-31.
25. Poole A R, Mort J S, Roughley P J (1993). Methods for evaluating mechanisms of cartilage breakdown. In Woessner J F Jr Howell DS (Eds.). *Cartilage Breakdown: Basic and Clinical Aspects*. Marcel Dekker, New York, pp: 225-260.
26. Radkiewicz, J. L., Zipse, H., Clarke, S., and Houk, K. N. (1996) Accelerated Racemization of Aspartic Acid and Asparagine Residues via Succinimide Intermediates: An ab Initio Theoretical Exploration of Mechanism J. Am. Chem. Soc. 118, 9148-9155.
27. Rafferty B, Coy DH and Poole S (1988) Pharmacokinetic evaluation of superactive analogues of growth hormone-releasing factor (1-29)-amide Peptides 9(1):207-9
28. Rosenberg K, Olson H, Morgelin M, Heinegård D. 1998. Cartilage Oligomeric Matrix Protein shows high affinity zinc-dependant interaction with triple helical collagen. J. Biol. Chem. 273, 20397-20403.
29. Saxne T, Heinegård D. (1992) Cartilage oligomeric matrix protein: A novel marker of cartilage turnover detectable in synovial fluid and blood. *Br. J. Rheumatol.* 31: 583-591.
30. Saxne T and Heinegård D (1995). Serum concentrations of two cartilage matrix proteins reflecting different aspects of cartilage turnover in relapsing polychondritis. *Arthritis Rheum.* 38:294-296
31. Van der Rest M and Garrone R (1991). Collagen family of proteins. *FASEB J* 5: 2814-2823.
32. Van Regenmortel M, and Muller S. (1998) D-peptides as immunogens and diagnostic reagents. Current opinion in Biotechnology, 9:377-382
33. Vilim V et al. Characterization of monoclonal antibodies recognizing different fragments of cartilage oligomeric matrix protein in human body fluids. Arch Biochem Biophys. 1997, 341, 8-16
34. Vingsbo-Lundberg C, Saxne T, Olsson H, Holmdahl R Increased serum levels of cartilage oligomeric matrix protein in chronic erosive arthritis in rats. Arthritis Rheum. 1998, 41, 544-550
35. Wollheim, F. A. (1996). Predictors of joint damage in rheumatoid arthritis. *APMIS* 104: 81-93.
36. Sakai L Y, Keene D R, Engvall E.(1986) Fibrillin, A New 350-Kd Glycoprotein, Is A Component Of Extracellular Microfibrils. J Cell Biol 1986 December;103(6 Pt 1):2499-509
37. Keene D R, Jordan C D, Reinhardt D P, Ridgway C C, Ono R N, Corson G M, Fairhurst M, Sussman M D, Memoli V A, Sakai L Y.(1997) Fibrillin-1 in human cartilage: developmental expression and formation of special banded fibers. J Histochem Cytochem. 1997 August;45(8):1069-82.
38. Zhang H, Hu W, Ramirez F.(1995) Developmental expression of fibrillin genes suggests heterogeneity of extracellular microfibrils. J Cell Biol 1995 May;129(4): 1165-76
39. DiDonato A, Ciardello M A, de Nigris M, Piccoli R, Mazzarella L, and Alessio G (1993) J Biol Chem 268: 4745-4751.

40. Stevenson C L, Anderegg R J and Borchardt R T (1993) J Pharm Biomed Anal 11: 367-373.
41. Aswad D W, Johnson B A, Glass D B (1987) Biochemistry 26: 675-681.
42. Potter S M, Henzel W J and Aswad D W (1993) Protein Sci 2: 1648-1663.
43. Aswad D W and Guzzetta A W (1995) Methods for analysis of deamidation and isoaspartate formation in peptides and proteins. In "Deamidation and isoaspartate formation in peptides and proteins" Aswad D W (Ed.), CRC Series in anaytical Biotechnology, CRC Press, Boca Raton, Fla.; Chapter 2, pp.: 7-29.
44. Smyth D G, Stein W H and Moore S (1963) J Biol Chem 238: 227-234.

The disclosures of all references reported herein are incorporated by reference.

The invention has been described with particular reference to preferred embodiments thereof. However, it will be appreciated that those skilled in the art, upon consideration of this disclosure, may make modifications and improvements within the spirit and scope of the invention.

The invention claimed is

1. A method for measuring an amount of isomerised fragments of cartilage oligomeric matrix protein (COMP), comprising measuring in a sample of blood, serum, plasma, or synovial fluid the amount of isomerised fragments of COMP which comprise the amino acid sequence AQED$_\beta$SDH (SEQ ID NO 21) wherein the D residue at position 4 therein is L-aspartic acid bound in the peptide chain via the β carboxylic acid thereof, said measurement being carried out using an antibody or binding fragment of an antibody which specifically recognizes and binds said sequence and which preferentially binds said sequence AQED$_\beta$SDH (SEQ ID NO 21) as compared to the non-isomerised COMP fragment containing the sequence AQEDSDH (SEQ ID NO 22) in which the D residue at position 4 therein is bound in the peptide chain via the α carboxylic acid group thereof.

2. A method as claimed in claim 1, wherein said antibody or binding fragment of an antibody is an antibody raised against a synthetic peptide having an amino acid sequence comprising AQED$_\beta$SDH (SEQ ID NO 21), or is a binding fragment of a said antibody.

3. A method as claimed in claim 2, wherein said antibody has been raised against a synthetic peptide having an amino acid sequence of COMP containing AQED$_\beta$SDH (SEQ ID NO 21).

4. A method as claimed in claim 1, wherein said measurement provides an index of cartilage turnover relevant for conditions and diseases affecting joint tissue turnover.

5. A method as claimed in claim 4, wherein said measurement provides an index indicative of cartilage turnover in a patient suffering from osteoarthritis or rheumatoid arthritis.

* * * * *

SEQUENCE LISTING

<160> NUMBER OF SEQ ID NOS: 20

<210> SEQ ID NO 1
<211> LENGTH: 4391
<212> TYPE: PRT
<213> ORGANISM: Perlecan Homo sapiens
<300> PUBLICATION INFORMATION:
<308> DATABASE ACCESSION NUMBER: AAA52700
<309> DATABASE ENTRY DATE: 1994-11-08

<400> SEQUENCE: 1

```
Met Gly Trp Arg Ala Pro Gly Ala Leu Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Tyr Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
    130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190

Pro Gln Phe Pro Arg Ala Cys Thr Glu Ala Glu Phe Ala Cys His Ser
        195                 200                 205

Tyr Asn Glu Cys Val Ala Leu Glu Tyr Arg Cys Asp Arg Arg Pro Asp
    210                 215                 220

Cys Arg Asp Met Ser Asp Glu Leu Asn Cys Glu Glu Pro Val Leu Gly
225                 230                 235                 240

Ile Ser Pro Thr Phe Ser Leu Leu Val Glu Thr Thr Ser Leu Pro Pro
                245                 250                 255

Arg Pro Glu Thr Thr Ile Met Arg Gln Pro Pro Val Thr His Ala Pro
```

```
                    260                 265                 270
Gln Pro Leu Leu Pro Gly Ser Val Arg Pro Leu Pro Cys Gly Pro Gln
            275                 280                 285

Glu Ala Ala Cys Arg Asn Gly His Cys Ile Pro Arg Asp Tyr Leu Cys
        290                 295                 300

Asp Gly Gln Glu Asp Cys Glu Asp Gly Ser Asp Glu Leu Asp Cys Gly
305                 310                 315                 320

Pro Pro Pro Pro Cys Glu Pro Asn Glu Phe Pro Cys Gly Asn Gly His
                325                 330                 335

Cys Ala Leu Lys Leu Trp Arg Cys Asp Gly Asp Phe Asp Cys Glu Asp
            340                 345                 350

Arg Thr Asp Glu Ala Asn Cys Pro Thr Lys Arg Pro Glu Glu Val Cys
        355                 360                 365

Gly Pro Thr Gln Phe Arg Cys Val Ser Thr Asn Met Cys Ile Pro Ala
    370                 375                 380

Ser Phe His Cys Asp Glu Glu Ser Asp Cys Pro Asp Arg Ser Asp Glu
385                 390                 395                 400

Phe Gly Cys Met Pro Pro Gln Val Val Thr Pro Pro Arg Glu Ser Ile
                405                 410                 415

Gln Ala Ser Arg Gly Gln Thr Val Thr Phe Thr Cys Val Ala Ile Gly
            420                 425                 430

Val Pro Thr Pro Ile Ile Asn Trp Arg Leu Asn Trp Gly His Ile Pro
        435                 440                 445

Ser His Pro Arg Val Thr Val Thr Ser Glu Gly Gly Arg Gly Thr Leu
    450                 455                 460

Ile Ile Arg Asp Val Lys Glu Ser Asp Gln Gly Ala Tyr Thr Cys Glu
465                 470                 475                 480

Ala Met Asn Ala Arg Gly Met Val Phe Gly Ile Pro Asp Gly Val Leu
                485                 490                 495

Glu Leu Val Pro Gln Arg Gly Pro Cys Pro Asp Gly His Phe Tyr Leu
            500                 505                 510

Glu His Ser Ala Ala Cys Leu Pro Cys Phe Cys Phe Gly Ile Thr Ser
        515                 520                 525

Val Cys Gln Ser Thr Arg Arg Phe Arg Asp Gln Ile Arg Leu Arg Phe
    530                 535                 540

Asp Gln Pro Asp Asp Phe Lys Gly Val Asn Val Thr Met Pro Ala Gln
545                 550                 555                 560

Pro Gly Thr Pro Pro Leu Ser Ser Thr Gln Leu Gln Ile Asp Pro Ser
                565                 570                 575

Leu His Glu Phe Gln Leu Val Asp Leu Ser Arg Arg Phe Leu Val His
            580                 585                 590

Asp Ser Phe Trp Ala Leu Pro Glu Gln Phe Leu Gly Asn Lys Val Asp
        595                 600                 605

Ser Tyr Gly Gly Ser Leu Arg Tyr Asn Val Arg Tyr Glu Leu Ala Arg
    610                 615                 620

Gly Met Leu Glu Pro Val Gln Arg Pro Asp Val Val Leu Val Gly Ala
625                 630                 635                 640

Gly Tyr Arg Leu Leu Ser Arg Gly His Thr Pro Thr Gln Pro Gly Ala
                645                 650                 655

Leu Asn Gln Arg Gln Val Gln Phe Ser Glu Glu His Trp Val His Glu
            660                 665                 670

Ser Gly Arg Pro Val Gln Arg Ala Glu Leu Leu Gln Val Leu Gln Ser
        675                 680                 685
```

```
Leu Glu Ala Val Leu Ile Gln Thr Val Tyr Asn Thr Lys Met Ala Ser
    690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
            725                 730                 735

Tyr Ser Gly Leu Ser Cys Glu Ser Cys Asp Ala His Phe Thr Arg Val
                740                 745                 750

Pro Gly Gly Pro Tyr Leu Gly Thr Cys Ser Gly Cys Ser Cys Asn Gly
            755                 760                 765

His Ala Ser Ser Cys Asp Pro Val Tyr Gly His Cys Leu Asn Cys Gln
770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
                805                 810                 815

Pro Tyr Ile Asp Ala Ser Arg Arg Phe Ser Asp Thr Cys Phe Leu Asp
            820                 825                 830

Thr Asp Gly Gln Ala Thr Cys Asp Ala Cys Ala Pro Gly Tyr Thr Gly
            835                 840                 845

Arg Arg Cys Glu Ser Cys Ala Pro Gly Tyr Glu Gly Asn Pro Ile Gln
850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                885                 890                 895

Asn Val Val Gly Arg Leu Cys Asn Glu Cys Ala Asp Gly Ser Phe His
                900                 905                 910

Leu Ser Thr Arg Asn Pro Asp Gly Cys Leu Lys Cys Phe Cys Met Gly
            915                 920                 925

Val Ser Arg His Cys Thr Ser Ser Ser Trp Ser Arg Ala Gln Leu His
            930                 935                 940

Gly Ala Ser Glu Glu Pro Gly His Phe Ser Leu Thr Asn Ala Ala Ser
945                 950                 955                 960

Thr His Thr Thr Asn Glu Gly Ile Phe Ser Pro Thr Pro Gly Glu Leu
                965                 970                 975

Gly Phe Ser Ser Phe His Arg Leu Leu Ser Gly Pro Tyr Phe Trp Ser
            980                 985                 990

Leu Pro Ser Arg Phe Leu Gly Asp Lys Val Thr Ser Tyr Gly Gly Glu
            995                 1000                1005

Leu Arg Phe Thr Val Thr Gln Arg Ser Gln Pro Gly Ser Thr Pro
    1010                1015                1020

Leu His Gly Gln Pro Leu Val Val Leu Gln Gly Asn Asn Ile Ile
    1025                1030                1035

Leu Glu His His Val Ala Gln Glu Pro Ser Pro Gly Gln Pro Ser
    1040                1045                1050

Thr Phe Ile Val Pro Phe Arg Glu Gln Ala Trp Gln Arg Pro Asp
    1055                1060                1065

Gly Gln Pro Ala Thr Arg Glu His Leu Leu Met Ala Leu Ala Gly
    1070                1075                1080

Ile Asp Thr Leu Leu Ile Arg Ala Ser Tyr Ala Gln Gln Pro Ala
    1085                1090                1095
```

-continued

```
Glu Ser Arg Val Ser Gly Ile Ser Met Asp Val Ala Val Pro Glu
1100                1105                1110

Glu Thr Gly Gln Asp Pro Ala Leu Glu Val Glu Gln Cys Ser Cys
1115                1120                1125

Pro Pro Gly Tyr Arg Gly Pro Ser Cys Gln Asp Cys Asp Thr Gly
1130                1135                1140

Tyr Thr Arg Thr Pro Ser Gly Leu Tyr Leu Gly Thr Cys Glu Arg
1145                1150                1155

Cys Ser Cys His Gly His Ser Glu Ala Cys Glu Pro Glu Thr Gly
1160                1165                1170

Ala Cys Gln Gly Cys Gln His His Thr Glu Gly Pro Arg Cys Glu
1175                1180                1185

Gln Cys Gln Pro Gly Tyr Tyr Gly Asp Ala Gln Arg Gly Thr Pro
1190                1195                1200

Gln Asp Cys Gln Leu Cys Pro Cys Tyr Gly Asp Pro Ala Ala Gly
1205                1210                1215

Gln Ala Ala His Thr Cys Phe Leu Asp Thr Asp Gly His Pro Thr
1220                1225                1230

Cys Asp Ala Cys Ser Pro Gly His Ser Gly Arg His Cys Glu Arg
1235                1240                1245

Cys Ala Pro Gly Tyr Tyr Gly Asn Pro Ser Gln Gly Gln Pro Cys
1250                1255                1260

Gln Arg Asp Ser Gln Val Pro Gly Pro Ile Gly Cys Asn Cys Asp
1265                1270                1275

Pro Gln Gly Ser Val Ser Ser Gln Cys Asp Ala Ala Gly Gln Cys
1280                1285                1290

Gln Cys Lys Ala Gln Val Glu Gly Leu Thr Cys Ser His Cys Arg
1295                1300                1305

Pro His His Phe His Leu Ser Ala Ser Asn Pro Asp Gly Cys Leu
1310                1315                1320

Pro Cys Phe Cys Met Gly Ile Thr Gln Gln Cys Ala Ser Ser Ala
1325                1330                1335

Tyr Thr Arg His Leu Ile Ser Thr His Phe Ala Pro Gly Asp Phe
1340                1345                1350

Gln Gly Phe Ala Leu Val Asn Pro Gln Arg Asn Ser Arg Leu Thr
1355                1360                1365

Gly Glu Phe Thr Val Glu Pro Val Pro Glu Gly Ala Gln Leu Ser
1370                1375                1380

Phe Gly Asn Phe Ala Gln Leu Gly His Glu Ser Phe Tyr Trp Gln
1385                1390                1395

Leu Pro Glu Thr Tyr Gln Gly Asp Lys Val Ala Ala Tyr Gly Gly
1400                1405                1410

Lys Leu Arg Tyr Thr Leu Ser Tyr Thr Ala Gly Pro Gln Gly Ser
1415                1420                1425

Pro Leu Ser Asp Pro Asp Val Gln Ile Thr Gly Asn Asn Ile Met
1430                1435                1440

Leu Val Ala Ser Gln Pro Ala Leu Gln Gly Pro Glu Arg Arg Ser
1445                1450                1455

Tyr Glu Ile Met Phe Arg Glu Glu Phe Trp Arg Arg Pro Asp Gly
1460                1465                1470

Gln Pro Ala Thr Arg Glu His Leu Leu Met Ala Leu Ala Asp Leu
1475                1480                1485

Asp Glu Leu Leu Ile Arg Ala Thr Phe Ser Ser Val Pro Leu Val
```

```
            1490                1495              1500

Ala Ser  Ile Ser Ala Val  Ser Leu Glu Val  Ala Gln Pro Gly Pro
    1505             1510              1515

Ser Asn  Arg Pro Arg Ala  Leu Glu Val Glu  Glu Cys Arg Cys Pro
    1520             1525              1530

Pro Gly  Tyr Ile Gly Leu  Ser Cys Gln Asp  Cys Ala Pro Gly Tyr
    1535             1540              1545

Thr Arg  Thr Gly Ser Gly  Leu Tyr Leu Gly  His Cys Glu Leu Cys
    1550             1555              1560

Glu Cys  Asn Gly His Ser  Asp Leu Cys His  Pro Glu Thr Gly Ala
    1565             1570              1575

Cys Ser  Gln Cys Gln His  Asn Ala Ala Gly  Glu Phe Cys Glu Leu
    1580             1585              1590

Cys Ala  Pro Gly Tyr Tyr  Gly Asp Ala Thr  Ala Gly Thr Pro Glu
    1595             1600              1605

Asp Cys  Gln Pro Cys Ala  Cys Pro Leu Thr  Asn Pro Glu Asn Met
    1610             1615              1620

Phe Ser  Arg Thr Cys Glu  Ser Leu Gly Ala  Gly Gly Tyr Arg Cys
    1625             1630              1635

Thr Ala  Cys Glu Pro Gly  Tyr Thr Gly Gln  Tyr Cys Glu Gln Cys
    1640             1645              1650

Gly Pro  Gly Tyr Val Gly  Asn Pro Ser Val  Gln Gly Gly Gln Cys
    1655             1660              1665

Leu Pro  Glu Thr Asn Gln  Ala Pro Leu Val  Val Glu Val His Pro
    1670             1675              1680

Ala Arg  Ser Ile Val Pro  Gln Gly Gly Ser  His Ser Leu Arg Cys
    1685             1690              1695

Gln Val  Ser Gly Ser Pro  Pro His Tyr Phe  Tyr Trp Ser Arg Glu
    1700             1705              1710

Asp Gly  Arg Pro Val Pro  Ser Gly Thr Gln  Gln Arg His Gln Gly
    1715             1720              1725

Ser Glu  Leu His Phe Pro  Ser Val Gln Pro  Ser Asp Ala Gly Val
    1730             1735              1740

Tyr Ile  Cys Thr Cys Arg  Asn Leu His Gln  Ser Asn Thr Ser Arg
    1745             1750              1755

Ala Glu  Leu Leu Val Thr  Glu Ala Pro Ser  Lys Pro Ile Thr Val
    1760             1765              1770

Thr Val  Glu Glu Gln Arg  Ser Gln Ser Val  Arg Pro Gly Ala Asp
    1775             1780              1785

Val Thr  Phe Ile Cys Thr  Ala Lys Ser Lys  Ser Pro Ala Tyr Thr
    1790             1795              1800

Leu Val  Trp Thr Arg Leu  His Asn Gly Lys  Leu Pro Thr Arg Ala
    1805             1810              1815

Met Asp  Phe Asn Gly Ile  Leu Thr Ile Arg  Asn Val Gln Leu Ser
    1820             1825              1830

Asp Ala  Gly Thr Tyr Val  Cys Thr Gly Ser  Asn Met Phe Ala Met
    1835             1840              1845

Asp Gln  Gly Thr Ala Thr  Leu His Val Gln  Ala Ser Gly Thr Leu
    1850             1855              1860

Ser Ala  Pro Val Val Ser  Ile His Pro Pro  Gln Leu Thr Val Gln
    1865             1870              1875

Pro Gly  Gln Leu Ala Glu  Phe Arg Cys Ser  Ala Thr Gly Ser Pro
    1880             1885              1890
```

-continued

```
Thr Pro Thr Leu Glu Trp Thr Gly Gly Pro Gly Gly Gln Leu Pro
    1895                1900                1905

Ala Lys Ala Gln Ile His Gly Gly Ile Leu Arg Leu Pro Ala Val
    1910                1915                1920

Glu Pro Thr Asp Gln Ala Gln Tyr Leu Cys Arg Ala His Ser Ser
    1925                1930                1935

Ala Gly Gln Gln Val Ala Arg Ala Val Leu His Val His Gly Gly
    1940                1945                1950

Gly Gly Pro Arg Val Gln Val Ser Pro Glu Arg Thr Gln Val His
    1955                1960                1965

Ala Gly Arg Thr Val Arg Leu Tyr Cys Arg Ala Ala Gly Val Pro
    1970                1975                1980

Ser Ala Thr Ile Thr Trp Arg Lys Glu Gly Gly Ser Leu Pro Pro
    1985                1990                1995

Gln Ala Arg Ser Glu Arg Thr Asp Ile Ala Thr Leu Leu Ile Pro
    2000                2005                2010

Ala Ile Thr Thr Ala Asp Ala Gly Phe Tyr Leu Cys Val Ala Thr
    2015                2020                2025

Ser Pro Ala Gly Thr Ala Gln Ala Arg Met Gln Val Val Val Leu
    2030                2035                2040

Ser Ala Ser Asp Ala Ser Pro Pro Gly Val Lys Ile Glu Ser Ser
    2045                2050                2055

Ser Pro Ser Val Thr Glu Gly Gln Thr Leu Asp Leu Asn Cys Val
    2060                2065                2070

Val Ala Gly Ser Ala His Ala Gln Val Thr Trp Tyr Arg Arg Gly
    2075                2080                2085

Gly Ser Leu Pro Pro His Thr Gln Val His Gly Ser Arg Leu Arg
    2090                2095                2100

Leu Pro Gln Val Ser Pro Ala Asp Ser Gly Glu Tyr Val Cys Arg
    2105                2110                2115

Val Glu Asn Gly Ser Gly Pro Lys Glu Ala Ser Ile Thr Val Ser
    2120                2125                2130

Val Leu His Gly Thr His Ser Gly Pro Ser Tyr Thr Pro Val Pro
    2135                2140                2145

Gly Ser Thr Arg Pro Ile Arg Ile Glu Pro Ser Ser Ser His Val
    2150                2155                2160

Ala Glu Gly Gln Thr Leu Asp Leu Asn Cys Val Val Pro Gly Gln
    2165                2170                2175

Ala His Ala Gln Val Thr Trp His Lys Arg Gly Gly Ser Leu Pro
    2180                2185                2190

Ala Arg His Gln Thr His Gly Ser Leu Leu Arg Leu His Gln Val
    2195                2200                2205

Thr Pro Ala Asp Ser Gly Glu Tyr Val Cys His Val Val Gly Thr
    2210                2215                2220

Ser Gly Pro Leu Glu Ala Ser Val Leu Val Thr Ile Glu Ala Ser
    2225                2230                2235

Val Ile Pro Gly Pro Ile Pro Pro Val Arg Ile Glu Ser Ser Ser
    2240                2245                2250

Ser Thr Val Ala Glu Gly Gln Thr Leu Asp Leu Ser Cys Val Val
    2255                2260                2265

Ala Gly Gln Ala His Ala Gln Val Thr Trp Tyr Lys Arg Gly Gly
    2270                2275                2280
```

-continued

Ser Leu Pro Ala Arg His Gln Val Arg Gly Ser Arg Leu Tyr Ile
2285                2290                2295

Phe Gln Ala Ser Pro Ala Asp Ala Gly Gln Tyr Val Cys Arg Ala
2300                2305                2310

Ser Asn Gly Met Glu Ala Ser Ile Thr Val Thr Val Thr Gly Thr
2315                2320                2325

Gln Gly Ala Asn Leu Ala Tyr Pro Ala Gly Ser Thr Gln Pro Ile
2330                2335                2340

Arg Ile Glu Pro Ser Ser Ser Gln Val Ala Glu Gly Gln Thr Leu
2345                2350                2355

Asp Leu Asn Cys Val Val Pro Gly Gln Ser His Ala Gln Val Thr
2360                2365                2370

Trp His Lys Arg Gly Gly Ser Leu Pro Val Arg His Gln Thr His
2375                2380                2385

Gly Ser Leu Leu Arg Leu Tyr Gln Ala Ser Pro Ala Asp Ser Gly
2390                2395                2400

Glu Tyr Val Cys Arg Val Leu Gly Ser Ser Val Pro Leu Glu Ala
2405                2410                2415

Ser Val Leu Val Thr Ile Glu Pro Ala Gly Ser Val Pro Ala Leu
2420                2425                2430

Gly Val Thr Pro Thr Val Arg Ile Glu Ser Ser Ser Ser Gln Val
2435                2440                2445

Ala Glu Gly Gln Thr Leu Asp Leu Asn Cys Leu Val Ala Gly Gln
2450                2455                2460

Ala His Ala Gln Val Thr Trp His Lys Arg Gly Gly Ser Leu Pro
2465                2470                2475

Ala Arg His Gln Val His Gly Ser Arg Leu Arg Leu Leu Gln Val
2480                2485                2490

Thr Pro Ala Asp Ser Gly Glu Tyr Val Cys Arg Val Val Gly Ser
2495                2500                2505

Ser Gly Thr Gln Glu Ala Ser Val Leu Val Thr Ile Gln Gln Arg
2510                2515                2520

Leu Ser Gly Ser His Ser Gln Gly Val Ala Tyr Pro Val Arg Ile
2525                2530                2535

Glu Ser Ser Ser Ala Ser Leu Ala Asn Gly His Thr Leu Asp Leu
2540                2545                2550

Asn Cys Leu Val Ala Ser Gln Ala Pro His Thr Ile Thr Trp Tyr
2555                2560                2565

Lys Arg Gly Gly Ser Leu Pro Ser Arg His Gln Ile Val Gly Ser
2570                2575                2580

Arg Leu Arg Ile Pro Gln Val Thr Pro Ala Asp Ser Gly Glu Tyr
2585                2590                2595

Val Cys His Val Ser Asn Gly Ala Gly Ser Arg Glu Thr Ser Leu
2600                2605                2610

Ile Val Thr Ile Gln Gly Ser Gly Ser Ser His Val Pro Ser Val
2615                2620                2625

Ser Pro Pro Ile Arg Ile Glu Ser Ser Ser Pro Thr Val Val Glu
2630                2635                2640

Gly Gln Thr Leu Asp Leu Asn Cys Val Val Ala Arg Gln Pro Gln
2645                2650                2655

Ala Ile Ile Thr Trp Tyr Lys Arg Gly Gly Ser Leu Pro Ser Arg
2660                2665                2670

His Gln Thr His Gly Ser His Leu Arg Leu His Gln Met Ser Val

-continued

```
              2675                2680                2685

Ala Asp  Ser Gly Glu Tyr  Val Cys Arg Ala  Asn Asn Ile Asp
    2690                2695                2700

Ala Leu  Glu Ala Ser Ile  Val Ile Ser Val  Ser Pro Ser Ala Gly
    2705                2710                2715

Ser Pro  Ser Ala Pro Gly  Ser Ser Met Pro  Ile Arg Ile Glu Ser
    2720                2725                2730

Ser Ser  Ser His Val Ala  Glu Gly Glu Thr  Leu Asp Leu Asn Cys
    2735                2740                2745

Val Val  Pro Gly Gln Ala  His Ala Gln Val  Thr Trp His Lys Arg
    2750                2755                2760

Gly Gly  Ser Leu Pro Ser  His His Gln Thr  Arg Gly Ser Arg Leu
    2765                2770                2775

Arg Leu  His His Val Ser  Pro Ala Asp Ser  Gly Glu Tyr Val Cys
    2780                2785                2790

Arg Val  Met Gly Ser Ser  Gly Pro Leu Glu  Ala Ser Val Leu Val
    2795                2800                2805

Thr Ile  Glu Ala Ser Gly  Ser Ser Ala Val  His Val Pro Ala Pro
    2810                2815                2820

Gly Gly  Ala Pro Pro Ile  Arg Ile Glu Pro  Ser Ser Arg Val
    2825                2830                2835

Ala Glu  Gly Gln Thr Leu  Asp Leu Lys Cys  Val Val Pro Gly Gln
    2840                2845                2850

Ala His  Ala Gln Val Thr  Trp His Lys Arg  Gly Gly Asn Leu Pro
    2855                2860                2865

Ala Arg  His Gln Val His  Gly Pro Leu Leu  Arg Leu Asn Gln Val
    2870                2875                2880

Ser Pro  Ala Asp Ser Gly  Glu Tyr Ser Cys  Gln Val Thr Gly Ser
    2885                2890                2895

Ser Gly  Thr Leu Glu Ala  Ser Val Leu Val  Thr Ile Glu Pro Ser
    2900                2905                2910

Ser Pro  Gly Pro Ile Pro  Ala Pro Gly Leu  Ala Gln Pro Ile Tyr
    2915                2920                2925

Ile Glu  Ala Ser Ser Ser  His Val Thr Glu  Gly Gln Thr Leu Asp
    2930                2935                2940

Leu Asn  Cys Val Val Pro  Gly Gln Ala His  Ala Gln Val Thr Trp
    2945                2950                2955

Tyr Lys  Arg Gly Gly Ser  Leu Pro Ala Arg  His Gln Thr His Gly
    2960                2965                2970

Ser Gln  Leu Arg Leu His  Leu Val Ser Pro  Ala Asp Ser Gly Glu
    2975                2980                2985

Tyr Val  Cys Arg Ala Ala  Ser Gly Pro Gly  Pro Glu Gln Glu Ala
    2990                2995                3000

Ser Phe  Thr Val Thr Val  Pro Pro Ser Glu  Gly Ser Ser Tyr Arg
    3005                3010                3015

Leu Arg  Ser Pro Val Ile  Ser Ile Asp Pro  Pro Ser Ser Thr Val
    3020                3025                3030

Gln Gln  Gly Gln Asp Ala  Ser Phe Lys Cys  Leu Ile His Asp Gly
    3035                3040                3045

Ala Ala  Pro Ile Ser Leu  Glu Trp Lys Thr  Arg Asn Gln Glu Leu
    3050                3055                3060

Glu Asp  Asn Val His Ile  Ser Pro Asn Gly  Ser Ile Ile Thr Ile
    3065                3070                3075
```

-continued

```
Val Gly Thr Arg Pro Ser Asn His Gly Thr Tyr Arg Cys Val Ala
3080            3085                3090

Ser Asn Ala Tyr Gly Val Ala Gln Ser Val Val Asn Leu Ser Val
3095                3100                3105

His Gly Pro Pro Thr Val Ser Val Leu Pro Glu Gly Pro Val Trp
3110                3115                3120

Val Lys Val Gly Lys Ala Val Thr Leu Glu Cys Val Ser Ala Gly
3125                3130                3135

Glu Pro Arg Ser Ser Ala Arg Trp Thr Arg Ile Ser Ser Thr Pro
3140                3145                3150

Ala Lys Leu Glu Gln Arg Thr Tyr Gly Leu Met Asp Ser His Ala
3155                3160                3165

Val Leu Gln Ile Ser Ser Ala Lys Pro Ser Asp Ala Gly Thr Tyr
3170                3175                3180

Val Cys Leu Ala Gln Asn Ala Leu Gly Thr Ala Gln Lys Gln Val
3185                3190                3195

Glu Val Ile Val Asp Thr Gly Ala Met Ala Pro Gly Ala Pro Gln
3200                3205                3210

Val Gln Ala Glu Glu Ala Glu Leu Thr Val Glu Ala Gly His Thr
3215                3220                3225

Ala Thr Leu Arg Cys Ser Ala Thr Gly Ser Pro Ala Pro Thr Ile
3230                3235                3240

His Trp Ser Lys Leu Arg Ser Pro Leu Pro Trp Gln His Arg Leu
3245                3250                3255

Glu Gly Asp Thr Leu Ile Ile Pro Arg Val Ala Gln Gln Asp Ser
3260                3265                3270

Gly Gln Tyr Ile Cys Asn Ala Thr Ser Pro Ala Gly His Ala Glu
3275                3280                3285

Ala Thr Ile Ile Leu His Val Glu Ser Pro Pro Tyr Ala Thr Thr
3290                3295                3300

Val Pro Glu His Ala Ser Val Gln Ala Gly Glu Thr Val Gln Leu
3305                3310                3315

Gln Cys Leu Ala His Gly Thr Pro Pro Leu Thr Phe Gln Trp Ser
3320                3325                3330

Arg Val Gly Ser Ser Leu Pro Gly Arg Ala Thr Ala Arg Asn Glu
3335                3340                3345

Leu Leu His Phe Glu Arg Ala Ala Pro Glu Asp Ser Gly Arg Tyr
3350                3355                3360

Arg Cys Arg Val Thr Asn Lys Val Gly Ser Ala Glu Ala Phe Ala
3365                3370                3375

Gln Leu Leu Val Gln Gly Pro Pro Gly Ser Leu Pro Ala Thr Ser
3380                3385                3390

Ile Pro Ala Gly Ser Thr Pro Thr Val Gln Val Thr Pro Gln Leu
3395                3400                3405

Glu Thr Lys Ser Ile Gly Ala Ser Val Glu Phe His Cys Ala Val
3410                3415                3420

Pro Ser Asp Gln Gly Thr Gln Leu Arg Trp Phe Lys Glu Gly Gly
3425                3430                3435

Gln Leu Pro Pro Gly His Ser Val Gln Asp Gly Val Leu Arg Ile
3440                3445                3450

Gln Asn Leu Asp Gln Ser Cys Gln Gly Thr Tyr Ile Cys Gln Ala
3455                3460                3465
```

-continued

| | | | | | | | | | | |
|---|---|---|---|---|---|---|---|---|---|---|
| His | Gly | Pro | Trp | Gly | Lys | Ala | Gln | Ala | Ser | Ala | Gln | Leu | Val | Ile |
| | 3470 | | | | 3475 | | | | 3480 | |
| Gln | Ala | Leu | Pro | Ser | Val | Leu | Ile | Asn | Ile | Arg | Thr | Ser | Val | Gln |
| | 3485 | | | | 3490 | | | | 3495 | |
| Thr | Val | Val | Val | Gly | His | Ala | Val | Glu | Phe | Glu | Cys | Leu | Ala | Leu |
| | 3500 | | | | 3505 | | | | 3510 | |
| Gly | Asp | Pro | Lys | Pro | Gln | Val | Thr | Trp | Ser | Lys | Val | Gly | Gly | His |
| | 3515 | | | | 3520 | | | | 3525 | |
| Leu | Arg | Pro | Gly | Ile | Val | Gln | Ser | Gly | Val | Val | Arg | Ile | Ala |
| | 3530 | | | | 3535 | | | | 3540 | |
| His | Val | Glu | Leu | Ala | Asp | Ala | Gly | Gln | Tyr | Arg | Cys | Thr | Ala | Thr |
| | 3545 | | | | 3550 | | | | 3555 | |
| Asn | Ala | Ala | Gly | Thr | Thr | Gln | Ser | His | Val | Leu | Leu | Leu | Val | Gln |
| | 3560 | | | | 3565 | | | | 3570 | |
| Ala | Leu | Pro | Gln | Ile | Ser | Met | Pro | Gln | Glu | Val | Arg | Val | Pro | Ala |
| | 3575 | | | | 3580 | | | | 3585 | |
| Gly | Ser | Ala | Ala | Val | Phe | Pro | Cys | Ile | Ala | Ser | Gly | Tyr | Pro | Thr |
| | 3590 | | | | 3595 | | | | 3600 | |
| Pro | Asp | Ile | Ser | Trp | Ser | Lys | Leu | Asp | Gly | Ser | Leu | Pro | Pro | Asp |
| | 3605 | | | | 3610 | | | | 3615 | |
| Ser | Arg | Leu | Glu | Asn | Asn | Met | Leu | Met | Leu | Pro | Ser | Val | Arg | Pro |
| | 3620 | | | | 3625 | | | | 3630 | |
| Gln | Asp | Ala | Gly | Thr | Tyr | Val | Cys | Thr | Ala | Thr | Asn | Arg | Gln | Gly |
| | 3635 | | | | 3640 | | | | 3645 | |
| Lys | Val | Lys | Ala | Phe | Ala | His | Leu | Gln | Val | Pro | Glu | Arg | Val | Val |
| | 3650 | | | | 3655 | | | | 3660 | |
| Pro | Tyr | Phe | Thr | Gln | Thr | Pro | Tyr | Ser | Phe | Leu | Pro | Leu | Pro | Thr |
| | 3665 | | | | 3670 | | | | 3675 | |
| Ile | Lys | Asp | Ala | Tyr | Arg | Lys | Phe | Glu | Ile | Lys | Ile | Thr | Phe | Arg |
| | 3680 | | | | 3685 | | | | 3690 | |
| Pro | Asp | Ser | Ala | Asp | Gly | Met | Leu | Leu | Tyr | Asn | Gly | Gln | Lys | Arg |
| | 3695 | | | | 3700 | | | | 3705 | |
| Val | Pro | Gly | Ser | Pro | Thr | Asn | Leu | Ala | Asn | Arg | Gln | Pro | Asp | Phe |
| | 3710 | | | | 3715 | | | | 3720 | |
| Ile | Ser | Phe | Gly | Leu | Val | Gly | Gly | Arg | Pro | Glu | Phe | Arg | Phe | Asp |
| | 3725 | | | | 3730 | | | | 3735 | |
| Ala | Gly | Ser | Gly | Met | Ala | Thr | Ile | Arg | His | Pro | Thr | Pro | Leu | Ala |
| | 3740 | | | | 3745 | | | | 3750 | |
| Leu | Gly | His | Phe | His | Thr | Val | Thr | Leu | Leu | Arg | Ser | Leu | Thr | Gln |
| | 3755 | | | | 3760 | | | | 3765 | |
| Gly | Ser | Leu | Ile | Val | Gly | Asp | Leu | Ala | Pro | Val | Asn | Gly | Thr | Ser |
| | 3770 | | | | 3775 | | | | 3780 | |
| Gln | Gly | Lys | Phe | Gln | Gly | Leu | Asp | Leu | Asn | Glu | Glu | Leu | Tyr | Leu |
| | 3785 | | | | 3790 | | | | 3795 | |
| Gly | Gly | Tyr | Pro | Asp | Tyr | Gly | Ala | Ile | Pro | Lys | Ala | Gly | Leu | Ser |
| | 3800 | | | | 3805 | | | | 3810 | |
| Ser | Gly | Phe | Ile | Gly | Cys | Val | Arg | Glu | Leu | Arg | Ile | Gln | Gly | Glu |
| | 3815 | | | | 3820 | | | | 3825 | |
| Glu | Ile | Val | Phe | His | Asp | Leu | Asn | Leu | Thr | Ala | His | Gly | Ile | Ser |
| | 3830 | | | | 3835 | | | | 3840 | |
| His | Cys | Pro | Thr | Cys | Arg | Asp | Arg | Pro | Cys | Gln | Asn | Gly | Gly | Gln |
| | 3845 | | | | 3850 | | | | 3855 | |
| Cys | His | Asp | Ser | Glu | Ser | Ser | Ser | Tyr | Val | Cys | Val | Cys | Pro | Ala |

-continued

```
                  3860            3865             3870
Gly Phe Thr Gly Ser Arg Cys Glu His Ser Gln Ala Leu His Cys
    3875            3880            3885
His Pro Glu Ala Cys Gly Pro Asp Ala Thr Cys Val Asn Arg Pro
    3890            3895            3900
Asp Gly Arg Gly Tyr Thr Cys Arg Cys His Leu Gly Arg Ser Gly
    3905            3910            3915
Leu Arg Cys Glu Glu Gly Val Thr Val Thr Pro Ser Leu Ser
    3920            3925            3930
Gly Ala Gly Ser Tyr Leu Ala Leu Pro Ala Leu Thr Asn Thr His
    3935            3940            3945
His Glu Leu Arg Leu Asp Val Glu Phe Lys Pro Leu Ala Pro Asp
    3950            3955            3960
Gly Val Leu Leu Phe Ser Gly Gly Lys Ser Gly Pro Val Glu Asp
    3965            3970            3975
Phe Val Ser Leu Ala Met Val Gly Gly His Leu Glu Phe Arg Tyr
    3980            3985            3990
Glu Leu Gly Ser Gly Leu Ala Val Leu Arg Ser Ala Glu Pro Leu
    3995            4000            4005
Ala Leu Gly Arg Trp His Arg Val Ser Ala Glu Arg Leu Asn Lys
    4010            4015            4020
Asp Gly Ser Leu Arg Val Asn Gly Gly Arg Pro Val Leu Arg Ser
    4025            4030            4035
Ser Pro Gly Lys Ser Gln Gly Leu Asn Leu His Thr Leu Leu Tyr
    4040            4045            4050
Leu Gly Gly Val Glu Pro Ser Val Pro Leu Ser Pro Ala Thr Asn
    4055            4060            4065
Met Ser Ala His Phe Arg Gly Cys Val Gly Glu Val Ser Val Asn
    4070            4075            4080
Gly Lys Arg Leu Asp Leu Thr Tyr Ser Phe Leu Gly Ser Gln Gly
    4085            4090            4095
Ile Gly Gln Cys Tyr Asp Ser Ser Pro Cys Glu Arg Gln Pro Cys
    4100            4105            4110
Gln His Gly Ala Thr Cys Met Pro Ala Gly Glu Tyr Glu Phe Gln
    4115            4120            4125
Cys Leu Cys Arg Asp Gly Phe Lys Gly Asp Leu Cys Glu His Glu
    4130            4135            4140
Glu Asn Pro Cys Gln Leu Arg Glu Pro Cys Leu His Gly Gly Thr
    4145            4150            4155
Cys Gln Gly Thr Arg Cys Leu Cys Leu Pro Gly Phe Ser Gly Pro
    4160            4165            4170
Arg Cys Gln Gln Gly Ser Gly His Gly Ile Ala Glu Ser Asp Trp
    4175            4180            4185
His Leu Glu Gly Ser Gly Gly Asn Asp Ala Pro Gly Gln Tyr Gly
    4190            4195            4200
Ala Tyr Phe His Asp Asp Gly Phe Leu Ala Phe Pro Gly His Val
    4205            4210            4215
Phe Ser Arg Ser Leu Pro Glu Val Pro Glu Thr Ile Glu Leu Glu
    4220            4225            4230
Val Arg Thr Ser Thr Ala Ser Gly Leu Leu Leu Trp Gln Gly Val
    4235            4240            4245
Glu Val Gly Glu Ala Gly Gln Gly Lys Asp Phe Ile Ser Leu Gly
    4250            4255            4260
```

-continued

Leu Gln Asp Gly His Leu Val Phe Arg Tyr Gln Leu Gly Ser Gly
    4265                4270                4275

Glu Ala Arg Leu Val Ser Glu Asp Pro Ile Asn Asp Gly Glu Trp
    4280                4285                4290

His Arg Val Thr Ala Leu Arg Glu Gly Arg Gly Ser Ile Gln
    4295                4300                4305

Val Asp Gly Glu Glu Leu Val Ser Gly Arg Ser Pro Gly Pro Asn
    4310                4315                4320

Val Ala Val Asn Ala Lys Gly Ser Val Tyr Ile Gly Gly Ala Pro
    4325                4330                4335

Asp Val Ala Thr Leu Thr Gly Gly Arg Phe Ser Ser Gly Ile Thr
    4340                4345                4350

Gly Cys Val Lys Asn Leu Val Leu His Ser Ala Arg Pro Gly Ala
    4355                4360                4365

Pro Pro Pro Gln Pro Leu Asp Leu Gln His Arg Ala Gln Ala Gly
    4370                4375                4380

Ala Asn Thr Arg Pro Cys Pro Ser
    4385                4390

<210> SEQ ID NO 2
<211> LENGTH: 18
<212> TYPE: PRT
<213> ORGANISM: Perlecan residues 2534-2551 Homo sapiens

<400> SEQUENCE: 2

Tyr Pro Val Arg Ile Glu Ser Ser Ser Ala Ser Leu Ala Asn Gly His
1               5                   10                  15

Thr Leu

<210> SEQ ID NO 3
<211> LENGTH: 347
<212> TYPE: PRT
<213> ORGANISM: Decorin Homo sapiens
<300> PUBLICATION INFORMATION:
<308> DATABASE ACCESSION NUMBER: AAA52301
<309> DATABASE ENTRY DATE: 1994-11-07

<400> SEQUENCE: 3

Met Lys Ala Thr Ile Ile Leu Leu Leu Leu Ala Gln Val Ser Trp Ala
1               5                   10                  15

Gly Pro Phe Gln Gln Arg Gly Leu Phe Asp Phe Met Leu Glu Asp Glu
                20                  25                  30

Ala Ser Gly Ile Gly Pro Glu Val Pro Asp Asp Arg Asp Phe Glu Pro
            35                  40                  45

Ser Leu Gly Pro Val Cys Pro Phe Arg Cys Gln Cys His Leu Arg Val
        50                  55                  60

Val Gln Cys Ser Asp Leu Gly Leu Asp Lys Val Pro Lys Asp Leu Pro
65                  70                  75                  80

Pro Asp Thr Thr Leu Leu Asp Leu Gln Asn Asn Lys Ile Thr Glu Ile
                85                  90                  95

Lys Asp Gly Asp Phe Lys Asn Leu Lys Asn Leu His Ala Leu Ile Leu
            100                 105                 110

Val Asn Asn Lys Ile Ser Lys Val Ser Pro Gly Ala Phe Thr Pro Leu
        115                 120                 125

Val Lys Leu Glu Arg Leu Tyr Leu Ser Lys Asn Gln Leu Lys Glu Leu
    130                 135                 140

```
Pro Glu Lys Met Pro Lys Thr Leu Gln Glu Leu Arg Ala His Glu Asn
145                 150                 155                 160

Glu Ile Thr Lys Val Arg Lys Val Thr Phe Asn Gly Leu Asn Gln Met
            165                 170                 175

Ile Val Ile Glu Leu Gly Thr Asn Pro Leu Lys Ser Ser Gly Ile Glu
        180                 185                 190

Asn Gly Ala Phe Gln Gly Met Lys Lys Leu Ser Tyr Ile Arg Ile Ala
    195                 200                 205

Asp Thr Asn Ile Thr Ser Ile Pro Gln Gly Leu Pro Pro Ser Leu Thr
210                 215                 220

Glu Leu His Leu Asp Gly Asn Lys Ile Ser Arg Val Asp Ala Ala Ser
225                 230                 235                 240

Leu Lys Gly Leu Asn Asn Leu Ala Lys Leu Gly Leu Ser Phe Asn Ser
                245                 250                 255

Ile Ser Ala Val Asp Asn Gly Ser Leu Ala Asn Thr Pro His Leu Arg
            260                 265                 270

Glu Leu His Leu Asp Asn Asn Lys Leu Thr Arg Val Val Tyr Leu His
        275                 280                 285

Asn Asn Asn Ile Ser Val Val Gly Ser Ser Asp Phe Cys Pro Pro Gly
    290                 295                 300

His Asn Thr Lys Lys Ala Ser Tyr Ser Gly Val Ser Leu Phe Ser Asn
305                 310                 315                 320

Pro Val Gln Tyr Trp Glu Ile Gln Pro Ser Thr Phe Arg Cys Val Tyr
                325                 330                 335

Val Arg Ser Ala Ile Gln Leu Gly Asn Tyr Lys
            340                 345

<210> SEQ ID NO 4
<211> LENGTH: 23
<212> TYPE: PRT
<213> ORGANISM: Decorin residues 207-230 Homo sapiens

<400> SEQUENCE: 4

Ile Ala Asp Thr Asn Ile Thr Ser Ile Pro Gln Gly Leu Pro Pro Ser
1               5                   10                  15

Leu Thr Glu Leu Leu Asp Gly
            20

<210> SEQ ID NO 5
<211> LENGTH: 368
<212> TYPE: PRT
<213> ORGANISM: Biglycan Homo sapiens
<300> PUBLICATION INFORMATION:
<308> DATABASE ACCESSION NUMBER: AAH04244
<309> DATABASE ENTRY DATE: 2001-07-12

<400> SEQUENCE: 5

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80
```

```
Leu Lys Ser Val Pro Lys Glu Ile Ser Pro Asp Thr Thr Leu Leu Asp
                85                  90                  95
Leu Gln Asn Asn Asp Ile Ser Glu Leu Arg Lys Asp Asp Phe Lys Gly
            100                 105                 110
Leu Gln His Leu Tyr Ala Leu Val Leu Val Asn Asn Lys Ile Ser Lys
        115                 120                 125
Ile His Glu Lys Ala Phe Ser Pro Leu Arg Lys Leu Gln Lys Leu Tyr
    130                 135                 140
Ile Ser Lys Asn His Leu Val Glu Ile Pro Pro Asn Leu Pro Ser Ser
145                 150                 155                 160
Leu Val Glu Leu Arg Ile His Asp Asn Arg Ile Arg Lys Val Pro Lys
                165                 170                 175
Gly Val Phe Ser Gly Leu Arg Asn Met Asn Cys Ile Glu Met Gly Gly
            180                 185                 190
Asn Pro Leu Glu Asn Ser Gly Phe Glu Pro Gly Ala Phe Asp Gly Leu
        195                 200                 205
Lys Leu Asn Tyr Leu Arg Ile Ser Glu Ala Lys Leu Thr Gly Ile Pro
    210                 215                 220
Lys Asp Leu Pro Glu Thr Leu Asn Glu Leu His Leu Asp His Asn Lys
225                 230                 235                 240
Ile Gln Ala Ile Glu Leu Glu Asp Leu Leu Arg Tyr Ser Lys Leu Tyr
                245                 250                 255
Arg Leu Gly Leu Gly His Asn Gln Ile Arg Met Ile Glu Asn Gly Ser
            260                 265                 270
Leu Ser Phe Leu Pro Thr Leu Arg Glu Leu His Leu Asp Asn Asn Lys
        275                 280                 285
Leu Ala Arg Val Pro Ser Gly Leu Pro Asp Leu Lys Leu Leu Gln Val
    290                 295                 300
Val Tyr Leu His Ser Asn Asn Ile Thr Lys Val Gly Val Asn Asp Phe
305                 310                 315                 320
Cys Pro Met Gly Phe Gly Val Lys Arg Ala Tyr Tyr Asn Gly Ile Ser
                325                 330                 335
Leu Phe Asn Asn Pro Val Pro Tyr Trp Glu Val Gln Pro Ala Thr Phe
            340                 345                 350
Arg Cys Val Thr Asp Arg Leu Ala Ile Gln Phe Gly Asn Tyr Lys Lys
        355                 360                 365

<210> SEQ ID NO 6
<211> LENGTH: 13
<212> TYPE: PRT
<213> ORGANISM: Biglycan residues 27-39 Homo sapiens

<400> SEQUENCE: 6

Phe Thr Leu Asp Asp Gly Pro Phe Met Met Asn Asp Glu
1               5                   10

<210> SEQ ID NO 7
<211> LENGTH: 935
<212> TYPE: PRT
<213> ORGANISM: Protocadherin Homo sapiens
<300> PUBLICATION INFORMATION:
<308> DATABASE ACCESSION NUMBER: AAD43714
<309> DATABASE ENTRY DATE: 1999-07-22

<400> SEQUENCE: 7

Met Ala Asn Arg Leu Gln Arg Gly Asp Arg Ser Arg Leu Leu Leu Leu
1               5                   10                  15
```

-continued

```
Leu Cys Ile Phe Leu Gly Thr Leu Arg Gly Phe Arg Ala Arg Gln Ile
         20                  25                  30
Arg Tyr Ser Val Pro Glu Thr Glu Lys Gly Ser Phe Val Gly Asn
         35                  40                  45
Ile Ser Lys Asp Leu Gly Leu Glu Pro Arg Glu Leu Ala Lys Arg Gly
         50                  55                  60
Val Arg Ile Val Ser Arg Gly Lys Thr Gln Leu Phe Ala Val Asn Pro
65                  70                  75                  80
Arg Ser Gly Ser Leu Ile Thr Ala Gly Arg Ile Asp Arg Glu Glu Leu
                 85                  90                  95
Cys Glu Thr Val Ser Ser Cys Phe Leu Asn Met Glu Leu Leu Val Glu
                100                 105                 110
Asp Thr Leu Lys Ile Tyr Gly Val Glu Val Glu Ile Ile Asp Ile Asn
                115                 120                 125
Asp Asn Ala Pro Ser Phe Gln Glu Asp Glu Val Glu Ile Lys Val Ser
        130                 135                 140
Glu His Ala Ile Pro Gly Ala Arg Phe Ala Leu Pro Asn Ala Arg Asp
145                 150                 155                 160
Pro Asp Val Gly Val Asn Ser Leu Gln Ser Tyr Gln Leu Ser Pro Asn
                165                 170                 175
Asn Tyr Phe Ser Leu Gln Leu Arg Gly Arg Thr Asp Gly Ala Lys Asn
                180                 185                 190
Pro Glu Leu Val Leu Glu Gly Ser Leu Asp Arg Glu Lys Glu Ala Ala
                195                 200                 205
His Leu Leu Leu Leu Thr Ala Leu Asp Gly Gly Asp Pro Ile Arg Lys
        210                 215                 220
Gly Ala Val Pro Ile Arg Val Val Val Leu Asp Val Asn Asp His Ile
225                 230                 235                 240
Pro Met Phe Thr Gln Ser Val Tyr Arg Val Ser Val Pro Glu Asn Ile
                245                 250                 255
Ser Ser Gly Thr Arg Val Leu Met Val Asn Ala Thr Asp Pro Asp Glu
                260                 265                 270
Gly Ile Asn Gly Glu Val Met Tyr Ser Phe Arg Asn Met Glu Ser Lys
                275                 280                 285
Ala Ser Glu Ile Phe Gln Leu Asp Ser Gln Thr Gly Glu Val Gln Val
        290                 295                 300
Arg Gly Ser Leu Asp Phe Glu Lys Tyr Arg Phe Tyr Glu Met Glu Ile
305                 310                 315                 320
Gln Gly Gln Asp Gly Gly Gly Leu Phe Thr Thr Thr Met Leu Ile
                325                 330                 335
Thr Val Val Asp Val Asn Asp Asn Ala Pro Glu Ile Thr Ile Thr Ser
                340                 345                 350
Ser Ile Asn Ser Ile Leu Glu Asn Ser Pro Pro Gly Thr Val Ile Ala
                355                 360                 365
Leu Leu Asn Val Gln Asp Gln Asp Ser Gly Glu Asn Gly Gln Val Ser
        370                 375                 380
Cys Phe Ile Pro Asn His Leu Pro Phe Lys Leu Glu Lys Thr Tyr Gly
385                 390                 395                 400
Asn Tyr Tyr Lys Leu Ile Thr Ser Arg Val Leu Asp Arg Glu Leu Val
                405                 410                 415
Gln Ser Tyr Asn Ile Thr Leu Thr Ala Thr Asp Gln Gly Ser Pro Pro
                420                 425                 430
Leu Ser Ala Glu Thr His Val Trp Leu Asn Val Ala Asp Asp Asn Asp
```

-continued

```
            435                 440                 445
Asn Pro Val Phe Pro His Ser Ser Tyr Ser Ala Tyr Ile Pro Glu
    450                 455                 460
Asn Asn Pro Arg Gly Ala Ser Ile Phe Ser Val Thr Ala Leu Asp Pro
465                 470                 475                 480
Asp Ser Lys Gln Asn Ala Leu Val Thr Tyr Ser Leu Thr Asp Asp Thr
            485                 490                 495
Val Gln Gly Val Pro Leu Ser Ser Tyr Val Ser Ile Asn Ser Asn Thr
        500                 505                 510
Gly Val Leu Tyr Ala Leu Gln Ser Phe Asp Tyr Glu Gln Phe Arg Asp
        515                 520                 525
Leu Glu Leu Arg Val Ile Ala Arg Asp Ser Gly Asp Pro Pro Leu Ser
    530                 535                 540
Ser Asn Val Ser Leu Ser Leu Phe Val Leu Asp Gln Asn Asp Asn Ala
545                 550                 555                 560
Pro Glu Ile Leu Tyr Pro Ala Leu Pro Thr Asp Gly Ser Thr Gly Val
            565                 570                 575
Glu Leu Ala Pro Arg Ser Ala Glu Pro Gly Tyr Leu Val Thr Lys Val
        580                 585                 590
Val Ala Val Asp Lys Asp Ser Gly Gln Asn Ala Trp Leu Ser Tyr Arg
    595                 600                 605
Leu Leu Lys Ala Ser Glu Pro Gly Leu Phe Ala Val Gly Glu His Thr
    610                 615                 620
Gly Glu Val Arg Thr Ala Arg Ala Leu Leu Asp Arg Asp Ala Leu Lys
625                 630                 635                 640
Gln Ser Leu Val Val Ala Val Gln Asp His Gly Gln Pro Pro Leu Ser
            645                 650                 655
Ala Thr Val Thr Leu Thr Val Ala Val Ala Asp Ser Ile Pro Glu Val
            660                 665                 670
Leu Ala Asp Leu Gly Ser Leu Glu Ser Leu Ala Asn Ser Glu Thr Ser
        675                 680                 685
Asp Leu Ser Leu Tyr Leu Val Val Ala Val Ala Val Ser Cys Ile
    690                 695                 700
Phe Leu Val Phe Val Ile Val Leu Leu Ala Leu Arg Leu Trp Arg Trp
705                 710                 715                 720
His Lys Ser Arg Leu Leu Gln Ala Ser Glu Gly Gly Leu Ala Gly Met
            725                 730                 735
Pro Thr Ser His Phe Val Gly Val Asp Gly Val Gln Ala Phe Leu Gln
            740                 745                 750
Thr Tyr Ser His Glu Val Ser Leu Ile Ala Asp Ser Gln Lys Ser His
            755                 760                 765
Leu Ile Phe Pro Gln Pro Asn Tyr Gly Asp Thr Leu Ile Ser Gln Glu
    770                 775                 780
Ser Cys Glu Lys Ser Glu Pro Leu Leu Ile Ala Glu Asp Ser Ala Ile
785                 790                 795                 800
Ile Leu Gly Lys Cys Asp Pro Thr Ser Asn Gln Gln Ala Pro Pro Asn
            805                 810                 815
Thr Asp Trp Arg Phe Ser Gln Ala Gln Arg Pro Gly Thr Ser Gly Ser
            820                 825                 830
Gln Asn Gly Asp Asp Thr Gly Thr Trp Pro Asn Asn Gln Phe Asp Thr
        835                 840                 845
Glu Met Leu Gln Ala Met Ile Leu Ala Ser Ala Ser Glu Ala Ala Asp
    850                 855                 860
```

```
Gly Ser Ser Thr Leu Gly Gly Ala Gly Thr Met Gly Leu Ser Ala
865                 870                 875                 880

Arg Tyr Gly Pro Gln Phe Thr Leu Gln His Val Pro Asp Tyr Arg Gln
                885                 890                 895

Asn Val Tyr Ile Pro Gly Ser Asn Ala Thr Leu Thr Asn Ala Ala Gly
            900                 905                 910

Lys Arg Asp Gly Lys Ala Pro Ala Gly Gly Asn Gly Asn Lys Lys Lys
            915                 920                 925

Ser Gly Lys Lys Glu Lys Lys
    930                 935

<210> SEQ ID NO 8
<211> LENGTH: 16
<212> TYPE: PRT
<213> ORGANISM: protocadherin residues 523-538 Homo sapiens

<400> SEQUENCE: 8

Tyr Glu Gln Phe Arg Asp Leu Glu Leu Arg Val Ile Ala Arg Asp Ser
1               5                   10                  15

<210> SEQ ID NO 9
<211> LENGTH: 10
<212> TYPE: PRT
<213> ORGANISM: protocadherin residues 523-532 Homo sapiens

<400> SEQUENCE: 9

Tyr Glu Gln Phe Arg Asp Leu Glu Leu Arg
1               5                   10

<210> SEQ ID NO 10
<211> LENGTH: 3002
<212> TYPE: PRT
<213> ORGANISM: Fibrillin-1 Homo sapiens
<300> PUBLICATION INFORMATION:
<308> DATABASE ACCESSION NUMBER: A47221
<309> DATABASE ENTRY DATE: 2000-07-21

<400> SEQUENCE: 10

Tyr Phe Ser Arg Glu Lys Pro Leu Arg Gly Arg Tyr Leu Lys Arg Trp
1               5                   10                  15

Gly Lys Glu Gly Ala Ala Gly Ala Ala Ala Glu Thr Val Gly Ala Thr
                20                  25                  30

Ser Gly Gln Glu Pro Gln Leu Gly Gln Leu Arg Ala Glu Pro Ser Ser
            35                  40                  45

Gly Cys Ser Gly His Asp Trp Glu Gln Pro Pro Pro Pro Arg Glu
        50                  55                  60

Ser Glu Pro Pro Leu Leu His Trp Gln Gly Pro Pro Glu Val Gly Ala
65                  70                  75                  80

Ala Pro Gly Glu Gly Gly Arg Ser Pro Ala Arg Gly Thr Gly Gly Gly
                85                  90                  95

Ile Ala Gly Pro Arg Arg Gly Ala Leu Gln Gly Ala Ala Ala
            100                 105                 110

Ala Asp Arg Ala Pro Gly Ala Ala Arg Gly Gly Gly Ser Arg Trp Arg
            115                 120                 125

Leu Gly Ile Met Arg Arg Gly Arg Leu Leu Glu Ile Ala Leu Gly Phe
            130                 135                 140

Thr Val Leu Leu Ala Ser Tyr Thr Ser His Gly Ala Asp Ala Asn Leu
145                 150                 155                 160
```

-continued

```
Glu Ala Gly Asn Val Lys Glu Thr Arg Ala Ser Arg Ala Lys Arg Arg
                165                 170                 175
Gly Gly Gly Gly His Asp Ala Leu Lys Gly Pro Asn Val Cys Gly Ser
            180                 185                 190
Arg Tyr Asn Ala Tyr Cys Cys Pro Gly Trp Lys Thr Leu Pro Gly Gly
        195                 200                 205
Asn Gln Cys Ile Val Pro Ile Cys Arg His Ser Cys Gly Asp Gly Phe
    210                 215                 220
Cys Ser Arg Pro Asn Met Cys Thr Cys Pro Ser Gly Gln Ile Ala Pro
225                 230                 235                 240
Ser Cys Gly Ser Arg Ser Ile Gln His Cys Asn Ile Arg Cys Met Asn
                245                 250                 255
Gly Gly Ser Cys Ser Asp Asp His Cys Leu Cys Gln Lys Gly Tyr Ile
            260                 265                 270
Gly Thr His Cys Gly Gln Pro Val Cys Glu Ser Gly Cys Leu Asn Gly
        275                 280                 285
Gly Arg Cys Val Ala Pro Asn Arg Cys Ala Cys Thr Tyr Gly Phe Thr
    290                 295                 300
Gly Pro Gln Cys Glu Arg Asp Tyr Arg Thr Gly Pro Cys Phe Thr Val
305                 310                 315                 320
Ile Ser Asn Gln Met Cys Gln Gly Gln Leu Ser Gly Ile Val Cys Thr
                325                 330                 335
Lys Gln Leu Cys Cys Ala Thr Val Gly Arg Ala Trp Gly His Pro Cys
            340                 345                 350
Glu Met Cys Pro Ala Gln Pro His Pro Cys Arg Arg Gly Phe Ile Pro
        355                 360                 365
Asn Ile Arg Thr Gly Ala Cys Gln Asp Val Asp Glu Cys Gln Ala Ile
    370                 375                 380
Pro Gly Leu Cys Gln Gly Gly Asn Cys Ile Asn Thr Val Gly Ser Phe
385                 390                 395                 400
Glu Cys Lys Cys Pro Ala Gly His Lys Leu Asn Glu Val Ser Gln Lys
                405                 410                 415
Cys Glu Asp Ile Asp Glu Cys Ser Thr Ile Pro Gly Ile Cys Glu Gly
            420                 425                 430
Gly Glu Cys Thr Asn Thr Val Ser Ser Tyr Phe Cys Lys Cys Pro Pro
        435                 440                 445
Gly Phe Tyr Thr Ser Pro Asp Gly Thr Arg Cys Ile Asp Val Arg Pro
    450                 455                 460
Gly Tyr Cys Tyr Thr Ala Leu Thr Asn Gly Arg Cys Ser Asn Gln Leu
465                 470                 475                 480
Pro Gln Ser Ile Thr Lys Met Gln Cys Cys Cys Asp Ala Gly Arg Cys
                485                 490                 495
Trp Ser Pro Gly Val Thr Val Ala Pro Glu Met Cys Pro Ile Arg Ala
            500                 505                 510
Thr Glu Asp Phe Asn Lys Leu Cys Ser Val Pro Met Val Ile Pro Gly
        515                 520                 525
Arg Pro Glu Tyr Pro Pro Pro Leu Gly Pro Ile Pro Pro Val Leu
    530                 535                 540
Pro Val Pro Pro Gly Phe Pro Gly Pro Gln Ile Pro Val Pro Arg
545                 550                 555                 560
Pro Pro Val Glu Tyr Leu Tyr Pro Ser Arg Glu Pro Pro Arg Val Leu
                565                 570                 575
Pro Val Asn Val Thr Asp Tyr Cys Gln Leu Val Arg Tyr Leu Cys Gln
```

-continued

```
            580                 585                 590
Asn Gly Arg Cys Ile Pro Thr Pro Gly Ser Tyr Arg Cys Glu Cys Asn
        595                 600                 605

Lys Gly Phe Gln Leu Asp Leu Arg Gly Glu Cys Ile Asp Val Asp Glu
        610                 615                 620

Cys Glu Lys Asn Pro Cys Ala Gly Gly Glu Cys Ile Asn Asn Gln Gly
625                 630                 635                 640

Ser Tyr Thr Cys Gln Cys Arg Ala Gly Tyr Gln Ser Thr Leu Thr Arg
                645                 650                 655

Thr Glu Cys Arg Asp Ile Asp Glu Cys Leu Gln Asn Gly Arg Ile Cys
            660                 665                 670

Asn Asn Gly Arg Cys Ile Asn Thr Asp Gly Ser Phe His Cys Val Cys
        675                 680                 685

Asn Ala Gly Phe His Val Thr Arg Asp Gly Lys Asn Cys Glu Asp Met
    690                 695                 700

Asp Glu Cys Ser Ile Arg Asn Met Cys Leu Asn Gly Met Cys Ile Asn
705                 710                 715                 720

Glu Asp Gly Ser Phe Lys Cys Ile Cys Lys Pro Gly Phe Gln Leu Ala
                725                 730                 735

Ser Asp Gly Arg Tyr Cys Lys Asp Ile Asn Glu Cys Glu Thr Pro Gly
            740                 745                 750

Ile Cys Met Asn Gly Arg Cys Val Asn Thr Asp Gly Ser Tyr Arg Cys
        755                 760                 765

Glu Cys Phe Pro Gly Leu Ala Val Gly Leu Asp Gly Arg Val Cys Val
    770                 775                 780

Asp Thr His Met Arg Ser Thr Cys Tyr Gly Gly Tyr Lys Arg Gly Gln
785                 790                 795                 800

Cys Ile Lys Pro Leu Phe Gly Ala Val Thr Lys Ser Glu Cys Cys Cys
                805                 810                 815

Ala Ser Thr Glu Tyr Ala Phe Gly Glu Pro Cys Gln Pro Cys Pro Ala
            820                 825                 830

Gln Asn Ser Ala Glu Tyr Gln Ala Leu Cys Ser Ser Gly Pro Gly Met
        835                 840                 845

Thr Ser Ala Gly Ser Asp Ile Asn Glu Cys Ala Leu Asp Pro Asp Ile
    850                 855                 860

Cys Pro Asn Gly Ile Cys Glu Asn Leu Arg Gly Thr Tyr Lys Cys Ile
865                 870                 875                 880

Cys Asn Ser Gly Tyr Glu Val Asp Ser Thr Gly Lys Asn Cys Val Asp
                885                 890                 895

Ile Asn Glu Cys Val Leu Asn Ser Leu Leu Cys Asp Asn Gly Gln Cys
            900                 905                 910

Arg Asn Thr Pro Gly Ser Phe Val Cys Thr Cys Pro Lys Gly Phe Ile
        915                 920                 925

Tyr Lys Pro Asp Leu Lys Thr Cys Glu Asp Ile Asp Glu Cys Glu Ser
    930                 935                 940

Ser Pro Cys Ile Asn Gly Val Cys Lys Asn Ser Pro Gly Ser Phe Ile
945                 950                 955                 960

Cys Glu Cys Ser Ser Glu Ser Thr Leu Asp Pro Thr Lys Thr Ile Cys
                965                 970                 975

Ile Glu Thr Ile Lys Gly Thr Cys Trp Gln Thr Val Ile Asp Gly Arg
            980                 985                 990

Cys Glu Ile Asn Ile Asn Gly Ala   Thr Leu Lys Ser Gln  Cys Cys Ser
        995                 1000                1005
```

-continued

```
Ser Leu Gly Ala Ala Trp Gly Ser Pro Cys Thr Leu Cys Gln Val
    1010                1015                1020

Asp Pro Ile Cys Gly Lys Gly Tyr Ser Arg Ile Lys Gly Thr Gln
    1025                1030                1035

Cys Glu Asp Ile Asp Glu Cys Glu Val Phe Pro Gly Val Cys Lys
    1040                1045                1050

Asn Gly Leu Cys Val Asn Thr Arg Gly Ser Phe Lys Cys Gln Cys
    1055                1060                1065

Pro Ser Gly Met Thr Leu Asp Ala Thr Gly Arg Ile Cys Leu Asp
    1070                1075                1080

Ile Arg Leu Glu Thr Cys Phe Leu Arg Tyr Glu Asp Glu Glu Cys
    1085                1090                1095

Thr Leu Pro Ile Ala Gly Arg His Arg Met Asp Ala Cys Cys Cys
    1100                1105                1110

Ser Val Gly Ala Ala Trp Gly Thr Glu Glu Cys Glu Glu Cys Pro
    1115                1120                1125

Met Arg Asn Thr Pro Glu Tyr Glu Glu Leu Cys Pro Arg Gly Pro
    1130                1135                1140

Gly Phe Ala Thr Lys Glu Ile Thr Asn Gly Lys Pro Phe Phe Lys
    1145                1150                1155

Asp Ile Asn Glu Cys Lys Met Ile Pro Ser Leu Cys Thr His Gly
    1160                1165                1170

Lys Cys Arg Asn Thr Ile Gly Ser Phe Lys Cys Arg Cys Asp Ser
    1175                1180                1185

Gly Phe Ala Leu Asp Ser Glu Glu Arg Asn Cys Thr Asp Ile Asp
    1190                1195                1200

Glu Cys Arg Ile Ser Pro Asp Leu Cys Gly Arg Gly Gln Cys Val
    1205                1210                1215

Asn Thr Pro Gly Asp Phe Glu Cys Lys Cys Asp Glu Gly Tyr Glu
    1220                1225                1230

Ser Gly Phe Met Met Met Lys Asn Cys Met Asp Ile Asp Glu Cys
    1235                1240                1245

Gln Arg Asp Pro Leu Leu Cys Arg Gly Gly Val Cys His Asn Thr
    1250                1255                1260

Glu Gly Ser Tyr Arg Cys Glu Cys Pro Pro Gly His Gln Leu Ser
    1265                1270                1275

Pro Asn Ile Ser Ala Cys Ile Asp Ile Asn Glu Cys Glu Leu Ser
    1280                1285                1290

Ala His Leu Cys Pro Asn Gly Arg Cys Val Asn Leu Ile Gly Lys
    1295                1300                1305

Tyr Gln Cys Ala Cys Asn Pro Gly Tyr His Ser Thr Pro Asp Arg
    1310                1315                1320

Leu Phe Cys Val Asp Ile Asp Glu Cys Ser Ile Met Asn Gly Gly
    1325                1330                1335

Cys Glu Thr Phe Cys Thr Asn Ser Glu Gly Ser Tyr Glu Cys Ser
    1340                1345                1350

Cys Gln Pro Gly Phe Ala Leu Met Pro Asp Gln Arg Ser Cys Thr
    1355                1360                1365

Asp Ile Asp Glu Cys Glu Asp Asn Pro Asn Ile Cys Asp Gly Gly
    1370                1375                1380

Gln Cys Thr Asn Ile Pro Gly Glu Tyr Arg Cys Leu Cys Tyr Asp
    1385                1390                1395
```

```
Gly Phe Met Ala Ser Glu Asp Met Lys Thr Cys Val Asp Val Asn
    1400                1405                1410

Glu Cys Asp Leu Asn Pro Asn Ile Cys Leu Ser Gly Thr Cys Glu
    1415                1420                1425

Asn Thr Lys Gly Ser Phe Ile Cys His Cys Asp Met Gly Tyr Ser
    1430                1435                1440

Gly Lys Lys Gly Lys Thr Gly Cys Thr Asp Ile Asn Glu Cys Glu
    1445                1450                1455

Ile Gly Ala His Asn Cys Gly Lys His Ala Val Cys Thr Asn Thr
    1460                1465                1470

Ala Gly Ser Phe Lys Cys Ser Cys Ser Pro Gly Trp Ile Gly Asp
    1475                1480                1485

Gly Ile Lys Cys Thr Asp Leu Asp Glu Cys Ser Asn Gly Thr His
    1490                1495                1500

Met Cys Ser Gln His Ala Asp Cys Lys Asn Thr Met Gly Ser Tyr
    1505                1510                1515

Arg Cys Leu Cys Lys Glu Gly Tyr Thr Gly Asp Gly Phe Thr Cys
    1520                1525                1530

Thr Asp Leu Asp Glu Cys Ser Glu Asn Leu Asn Leu Cys Gly Asn
    1535                1540                1545

Gly Gln Cys Leu Asn Ala Pro Gly Gly Tyr Arg Cys Glu Cys Asp
    1550                1555                1560

Met Gly Phe Val Pro Ser Ala Asp Gly Lys Ala Cys Glu Asp Ile
    1565                1570                1575

Asp Glu Cys Ser Leu Pro Asn Ile Cys Val Phe Gly Thr Cys His
    1580                1585                1590

Asn Leu Pro Gly Leu Phe Arg Cys Glu Cys Glu Ile Gly Tyr Glu
    1595                1600                1605

Leu Asp Arg Ser Gly Gly Asn Cys Thr Asp Val Asn Glu Cys Leu
    1610                1615                1620

Asp Pro Thr Thr Cys Ile Ser Gly Asn Cys Val Asn Thr Pro Gly
    1625                1630                1635

Ser Tyr Ile Cys Asp Cys Pro Pro Asp Phe Glu Leu Asn Pro Thr
    1640                1645                1650

Arg Val Gly Cys Val Asp Thr Arg Ser Gly Asn Cys Tyr Leu Asp
    1655                1660                1665

Ile Arg Pro Arg Gly Asp Asn Gly Asp Thr Ala Cys Ser Asn Glu
    1670                1675                1680

Ile Gly Val Gly Val Ser Lys Ala Ser Cys Cys Cys Ser Leu Gly
    1685                1690                1695

Lys Ala Trp Gly Thr Pro Cys Glu Met Cys Pro Ala Val Asn Thr
    1700                1705                1710

Ser Glu Tyr Lys Ile Leu Cys Pro Gly Gly Glu Gly Phe Arg Pro
    1715                1720                1725

Asn Pro Ile Thr Val Ile Leu Glu Asp Ile Asp Glu Cys Gln Glu
    1730                1735                1740

Leu Pro Gly Leu Cys Gln Gly Gly Lys Cys Ile Asn Thr Phe Gly
    1745                1750                1755

Ser Phe Gln Cys Arg Cys Pro Thr Gly Tyr Tyr Leu Asn Glu Asp
    1760                1765                1770

Thr Arg Val Cys Asp Asp Val Asn Glu Cys Glu Thr Pro Gly Ile
    1775                1780                1785

Cys Gly Pro Gly Thr Cys Tyr Asn Thr Val Gly Asn Tyr Thr Cys
```

```
                    1790                1795                1800

Ile Cys Pro Pro Asp Tyr Met Gln Val Asn Gly Gly Asn Asn Cys
    1805                1810                1815

Met Asp Met Arg Arg Ser Leu Cys Tyr Arg Asn Tyr Tyr Ala Asp
    1820                1825                1830

Asn Gln Thr Cys Asp Gly Glu Leu Leu Phe Asn Met Thr Lys Lys
    1835                1840                1845

Met Cys Cys Cys Ser Tyr Asn Ile Gly Arg Ala Trp Asn Lys Pro
    1850                1855                1860

Cys Glu Gln Cys Pro Ile Pro Ser Thr Asp Glu Phe Ala Thr Leu
    1865                1870                1875

Cys Gly Ser Gln Arg Pro Gly Phe Val Ile Asp Ile Tyr Thr Gly
    1880                1885                1890

Leu Pro Val Asp Ile Asp Glu Cys Arg Glu Ile Pro Gly Val Cys
    1895                1900                1905

Glu Asn Gly Val Cys Ile Asn Met Val Gly Ser Phe Arg Cys Glu
    1910                1915                1920

Cys Pro Val Gly Phe Phe Tyr Asn Asp Lys Leu Leu Val Cys Glu
    1925                1930                1935

Asp Ile Asp Glu Cys Gln Asn Gly Pro Val Cys Gln Arg Asn Ala
    1940                1945                1950

Glu Cys Ile Asn Thr Ala Gly Ser Tyr Arg Cys Asp Cys Lys Pro
    1955                1960                1965

Gly Tyr Arg Phe Thr Ser Thr Gly Gln Cys Asn Asp Arg Asn Glu
    1970                1975                1980

Cys Gln Glu Ile Pro Asn Ile Cys Ser His Gly Gln Cys Ile Asp
    1985                1990                1995

Thr Val Gly Ser Phe Tyr Cys Leu Cys His Thr Gly Phe Lys Thr
    2000                2005                2010

Asn Asp Asp Gln Thr Met Cys Leu Asp Ile Asn Glu Cys Glu Arg
    2015                2020                2025

Asp Ala Cys Gly Asn Gly Thr Cys Arg Asn Thr Ile Gly Ser Phe
    2030                2035                2040

Asn Cys Arg Cys Asn His Gly Phe Ile Leu Ser His Asn Asn Asp
    2045                2050                2055

Cys Ile Asp Val Asp Glu Cys Ala Ser Gly Asn Gly Asn Leu Cys
    2060                2065                2070

Arg Asn Gly Gln Cys Ile Asn Thr Val Gly Ser Phe Gln Cys Gln
    2075                2080                2085

Cys Asn Glu Gly Tyr Glu Val Ala Pro Asp Gly Arg Thr Cys Val
    2090                2095                2100

Asp Ile Asn Glu Cys Leu Leu Glu Pro Arg Lys Cys Ala Pro Gly
    2105                2110                2115

Thr Cys Gln Asn Leu Asp Gly Ser Tyr Arg Cys Ile Cys Pro Pro
    2120                2125                2130

Gly Tyr Ser Leu Gln Asn Glu Lys Cys Glu Asp Ile Asp Glu Cys
    2135                2140                2145

Val Glu Glu Pro Glu Ile Cys Ala Leu Gly Thr Cys Ser Asn Thr
    2150                2155                2160

Glu Gly Ser Phe Lys Cys Leu Cys Pro Glu Gly Phe Ser Leu Ser
    2165                2170                2175

Ser Ser Gly Arg Arg Cys Gln Asp Leu Arg Met Ser Tyr Cys Tyr
    2180                2185                2190
```

-continued

```
Ala Lys Phe Glu Gly Gly Lys Cys Ser Ser Pro Lys Ser Arg Asn
2195                2200                2205

His Ser Lys Gln Glu Cys Cys Ala Leu Lys Gly Glu Gly Trp
    2210                2215                2220

Gly Asp Pro Cys Glu Leu Cys Pro Thr Glu Pro Asp Glu Ala Phe
2225                2230                2235

Arg Gln Ile Cys Pro Tyr Gly Ser Gly Ile Ile Val Gly Pro Asp
    2240                2245                2250

Asp Ser Ala Val Asp Met Asp Glu Cys Lys Glu Pro Asp Val Cys
2255                2260                2265

Lys His Gly Gln Cys Ile Asn Thr Asp Gly Ser Tyr Arg Cys Glu
    2270                2275                2280

Cys Pro Phe Gly Tyr Thr Leu Ala Gly Asn Glu Cys Val Asp Thr
2285                2290                2295

Asp Glu Cys Ser Val Gly Asn Pro Cys Gly Asn Gly Thr Cys Lys
    2300                2305                2310

Asn Val Ile Gly Gly Phe Glu Cys Thr Cys Glu Glu Gly Phe Glu
2315                2320                2325

Pro Gly Pro Met Met Thr Cys Glu Asp Ile Asn Glu Cys Ala Gln
    2330                2335                2340

Asn Pro Leu Leu Cys Ala Phe Arg Cys Val Asn Thr Tyr Gly Ser
2345                2350                2355

Tyr Glu Cys Lys Cys Pro Val Gly Tyr Val Leu Arg Glu Asp Arg
    2360                2365                2370

Arg Met Cys Lys Asp Glu Asp Glu Cys Glu Glu Gly Lys His Asp
2375                2380                2385

Cys Thr Glu Lys Gln Met Glu Cys Lys Asn Leu Ile Gly Thr Tyr
    2390                2395                2400

Met Cys Ile Cys Gly Pro Gly Tyr Gln Arg Arg Pro Asp Gly Glu
2405                2410                2415

Gly Cys Val Asp Glu Asn Glu Cys Gln Thr Lys Pro Gly Ile Cys
    2420                2425                2430

Glu Asn Gly Arg Cys Leu Asn Thr Arg Gly Ser Tyr Thr Cys Glu
2435                2440                2445

Cys Asn Asp Gly Phe Thr Ala Ser Pro Asn Gln Asp Glu Cys Leu
    2450                2455                2460

Asp Asn Arg Glu Gly Tyr Cys Phe Thr Glu Val Leu Gln Asn Met
2465                2470                2475

Cys Gln Ile Gly Ser Ser Asn Arg Asn Pro Val Thr Lys Ser Glu
    2480                2485                2490

Cys Cys Cys Asp Gly Gly Arg Gly Trp Gly Pro His Cys Glu Ile
2495                2500                2505

Cys Pro Phe Gln Gly Thr Val Ala Phe Lys Lys Leu Cys Pro His
    2510                2515                2520

Gly Arg Gly Phe Met Thr Asn Gly Ala Asp Ile Asp Glu Cys Lys
2525                2530                2535

Val Ile His Asp Val Cys Arg Asn Gly Glu Cys Val Asn Asp Arg
    2540                2545                2550

Gly Ser Tyr His Cys Ile Cys Lys Thr Gly Tyr Thr Pro Asp Ile
2555                2560                2565

Thr Gly Thr Ser Cys Val Asp Leu Asn Glu Cys Asn Gln Ala Pro
2570                2575                2580
```

```
Lys Pro Cys Asn Phe Ile Cys Lys Asn Thr Glu Gly Ser Tyr Gln
2585                2590                2595

Cys Ser Cys Pro Lys Gly Tyr Ile Leu Gln Glu Asp Gly Arg Ser
    2600                2605                2610

Cys Lys Asp Leu Asp Glu Cys Ala Thr Lys Gln His Asn Cys Gln
2615                2620                2625

Phe Leu Cys Val Asn Thr Ile Gly Gly Phe Thr Cys Lys Cys Pro
2630                2635                2640

Pro Gly Phe Thr Gln His His Thr Ser Cys Ile Asp Asn Asn Glu
2645                2650                2655

Cys Thr Ser Asp Ile Asn Leu Cys Gly Ser Lys Gly Ile Cys Gln
2660                2665                2670

Asn Thr Pro Gly Ser Phe Thr Cys Glu Cys Gln Arg Gly Phe Ser
2675                2680                2685

Leu Asp Gln Thr Gly Ser Ser Cys Glu Asp Val Asp Glu Cys Glu
2690                2695                2700

Gly Asn His Arg Cys Gln His Gly Cys Gln Asn Ile Ile Gly Gly
2705                2710                2715

Tyr Arg Cys Ser Cys Pro Gln Gly Tyr Leu Gln His Tyr Gln Trp
2720                2725                2730

Asn Gln Cys Val Asp Glu Asn Glu Cys Leu Ser Ala His Ile Cys
2735                2740                2745

Gly Gly Ala Ser Cys His Asn Thr Leu Gly Ser Tyr Lys Cys Met
2750                2755                2760

Cys Pro Ala Gly Phe Gln Tyr Glu Gln Phe Ser Gly Gly Cys Gln
2765                2770                2775

Asp Ile Asn Glu Cys Gly Ser Ala Gln Ala Pro Cys Ser Tyr Gly
2780                2785                2790

Cys Ser Asn Thr Glu Gly Gly Tyr Leu Cys Gly Cys Pro Pro Gly
2795                2800                2805

Tyr Phe Arg Ile Gly Gln Gly His Cys Val Ser Gly Met Gly Met
2810                2815                2820

Gly Arg Gly Asn Pro Glu Pro Pro Val Ser Gly Glu Met Asp Asp
2825                2830                2835

Asn Ser Leu Ser Pro Glu Ala Cys Tyr Glu Cys Lys Ile Asn Gly
2840                2845                2850

Tyr Pro Lys Arg Gly Arg Lys Arg Arg Ser Thr Asn Glu Thr Asp
2855                2860                2865

Ala Ser Asn Ile Glu Asp Gln Ser Glu Thr Glu Ala Asn Val Ser
2870                2875                2880

Leu Ala Ser Trp Asp Val Glu Lys Thr Ala Ile Phe Ala Phe Asn
2885                2890                2895

Ile Ser His Val Ser Asn Lys Val Arg Ile Leu Glu Leu Leu Pro
2900                2905                2910

Ala Leu Thr Thr Leu Thr Asn His Asn Arg Tyr Leu Ile Glu Ser
2915                2920                2925

Gly Asn Glu Asp Gly Phe Phe Lys Ile Asn Gln Lys Glu Gly Ile
2930                2935                2940

Ser Tyr Leu His Phe Thr Lys Lys Lys Pro Val Ala Gly Thr Tyr
2945                2950                2955

Ser Leu Gln Ile Ser Ser Thr Pro Leu Tyr Lys Lys Lys Glu Leu
2960                2965                2970

Asn Gln Leu Glu Asp Lys Tyr Asp Lys Asp Tyr Leu Ser Gly Glu
```

```
                        2975                2980                2985

Leu Gly Asp Asn Leu Lys Met Lys Ile Gln Val Leu Leu His
        2990                2995                3000

<210> SEQ ID NO 11
<211> LENGTH: 13
<212> TYPE: PRT
<213> ORGANISM: Fibrillin-1 residues 2270-2782 Homo sapiens

<400> SEQUENCE: 11

Tyr Glu Gln Phe Ser Gly Gly Cys Gln Asp Ile Asn Glu
1               5                   10

<210> SEQ ID NO 12
<211> LENGTH: 14
<212> TYPE: PRT
<213> ORGANISM: Homo sapiens

<400> SEQUENCE: 12

Leu Tyr Pro Asn Gln Thr Gly Leu Pro Asp Pro Leu Ser Arg
1               5                   10

<210> SEQ ID NO 13
<211> LENGTH: 20
<212> TYPE: PRT
<213> ORGANISM: Homo sapiens

<400> SEQUENCE: 13

Ser Ala Ile Ile Ala Thr Glu Gln Leu Gln Ala Ala Tyr Glu Asp Gly
1               5                   10                  15

Phe His Gln Cys
            20

<210> SEQ ID NO 14
<211> LENGTH: 17
<212> TYPE: PRT
<213> ORGANISM: Homo sapiens

<400> SEQUENCE: 14

Leu Ala Thr Thr Gly Gln Leu Tyr Leu Ala Trp Gln Ala Gly Met Asp
1               5                   10                  15

Met

<210> SEQ ID NO 15
<211> LENGTH: 15
<212> TYPE: PRT
<213> ORGANISM: Homo sapiens

<400> SEQUENCE: 15

Thr Gly Glu Asp Phe Val Asp Ile Pro Glu Asn Phe Phe Gly Val
1               5                   10                  15

<210> SEQ ID NO 16
<211> LENGTH: 11
<212> TYPE: PRT
<213> ORGANISM: Homo sapiens

<400> SEQUENCE: 16

Thr Gly Glu Asp Phe Val Asp Ile Pro Glu Asn
1               5                   10

<210> SEQ ID NO 17
<211> LENGTH: 29
```

```
<212> TYPE: PRT
<213> ORGANISM: Homo sapiens

<400> SEQUENCE: 17

Val Ser Leu Pro Asn Tyr Pro Ala Ile Pro Ser Asp Ala Thr Leu Glu
1               5                   10                  15

Val Gln Ser Leu Arg Ser Asn Asp Ser Gly Val Tyr Arg
            20                  25

<210> SEQ ID NO 18
<211> LENGTH: 14
<212> TYPE: PRT
<213> ORGANISM: Homo sapiens
<220> FEATURE:
<221> NAME/KEY: MISC_FEATURE
<222> LOCATION: (4)..(10)
<223> OTHER INFORMATION: Xaa = any amino acid

<400> SEQUENCE: 18

Glu Gly Ser Xaa Gly Ala Asp Gly Pro Xaa Gly Arg Asp Gly
1               5                   10

<210> SEQ ID NO 19
<211> LENGTH: 7
<212> TYPE: PRT
<213> ORGANISM: Homo sapiens

<400> SEQUENCE: 19

Ala Gln Glu Asp Ser Asp His
1               5

<210> SEQ ID NO 20
<211> LENGTH: 10
<212> TYPE: PRT
<213> ORGANISM: Homo sapiens

<400> SEQUENCE: 20

Leu Leu Thr Gln Thr Asp Ser Asp Gly Arg
1               5                   10
```